US006949356B1

(12) United States Patent
Busby et al.

(10) Patent No.: US 6,949,356 B1
(45) Date of Patent: Sep. 27, 2005

(54) METHODS FOR IMPROVING SECONDARY METABOLITE PRODUCTION IN FUNGI

(75) Inventors: Robert Busby, Weymouth, MA (US); Brian Cali, Arlington, MA (US); Peter Hecht, Newton, MA (US); Doug Holtzman, Jamaica Plan, MA (US); Kevin Madden, Charlestown, MA (US); Mary Maxon, Somerville, MA (US); Todd Milne, Brookline, MA (US); Thea Norman, Belmont, MA (US); John Royer, Lexington, MA (US); Sofie Salama, Boston, MA (US); Amir Sherman, Boston, MA (US); Jeff Silva, Beverly, MA (US); Eric Summers, Brookline, MA (US)

(73) Assignee: Microbia, Inc., Cambridge, MA (US)

( * ) Notice: Subject to any disclaimer, the term of this patent is extended or adjusted under 35 U.S.C. 154(b) by 0 days.

(21) Appl. No.: 09/487,558

(22) Filed: Jan. 19, 2000

Related U.S. Application Data
(60) Provisional application No. 60/160,587, filed on Oct. 20, 1999.

(51) Int. Cl.[7] .............................. C12P 1/00; C12P 1/02

(52) U.S. Cl. ..................... 435/41; 435/43; 435/254.11; 435/471

(58) Field of Search ............................. 435/254.11, 41, 435/43, 471

(56) References Cited

U.S. PATENT DOCUMENTS
5,665,543 A    9/1997 Foulkes et al. ................. 435/6

FOREIGN PATENT DOCUMENTS
| EP | 357119 | | 8/1989 |
| WO | WO 99/25735 | | 5/1999 |
| WO | WO 99/25865 | * | 5/1999 |
| WO | WO 00/37629 | | 6/2000 |
| WO | WO 01/42426 A1 | | 12/2000 |

OTHER PUBLICATIONS

Pfeifer et al. Biosynthesis of polyketides in heterologous hosts. Microbiology and Molecular Biology Reviews: 106–118, Mar. 2001.*
Fillinger et al. FEBS Letters 368: 547–550, 1995.*
Chang et al., Cloning of the *Aspergillus parasiticus* apa–2 gene associated with the regualtion of aflatoxin biosynthesis; Appl Environ Microbiol 59:3273–3279 (1993).
Kennedy and Turner, alpha–(L–alpha Aminoadipyl)–L–cysteinyl–D–valine synthetase is a rate limiting enzyme for penicillin production in *Aspergillus nidulans*; Mol Gen Genet 253:189–197 (1996).

Theilgaard et al., Quantitative Analysis of Penicillium chrysogenum Wis54–1255 Transformants Overexpressing the Penicillin Biosynthetic Genes; Biotech Bioeng 72:379–388 (2001).
Tag et al., G–protein signalling mediates differential production of toxic secondary metabolites; Mol Microbiol 38:658–665 (2000).
Agathos, S.N. et al., "Physiological and Genetic Factors for Process Development of Cyclosporine Fermentations", J. Ind. Microbiol. 1:39–48 (1986).
Alarco, Anne–Marie et al., "AP1–mediated Multidrug Resistance in *Saccharomyces cerevisiae* Required FLR1 Encoding a Transporter of the Major Facilitator Superfamily", J. Biol. Chem. 272: 19304–13 (1997).
Alberts, A.W. et al., "Mevinolin: A Highly Potent Competitive Inhibitor of Hydroxymethylglutaryl–coenzyme A Reductase and a Cholesterol–lowering Agent", Proc. Nat. Sci. USA 77:3957–3961 (1980).
Alexander, N.J. et al. "TRI12, a Trichothecene Efflux Pump from *Fusarium sporotrichioides*: Gene Isolation and Expression in Yeast", Mol. Gen. Genet. 261:977–84 (1999).
Bartolomei, Marisa S. et al., "Genetic Analysis of the Repetitive Carbosyl–Terminal Domain of the Largest Subunit of Mouse RNA Polymerase II", Mol. Cell. Biol. 8:330–9 (1988).
Beltzer, James P. et al., "Yeast LEU4 Encodes Mitochondrial and Nonmitochondrial Forms of α–Isopropylmalate Synthase", J. Biol. Chem. 263: 368–74 (1988).
Bentley Ronald, "Secondary Metabolite Biosynthesis: The First Century", Crt. Rev. Biotechnol. 19:1–40 (1999).
Boret, J.F. edit., "Ciciosporin and its Future", Prog. Allergy 38:9–18 (1986).
Boyum, Rodney et al., "Effect of ATP Binding Cassette/ Multidrug Resistance Proteins on ATP Efflux of *Saccharomyces cerevisiae*", Biochem. Biophys. Res. Commun. 230:22–6 (1997).
Brakhage, Axel A., "Molecular Regulation of β–Lactam Biosynthesis in Filamentous Fungi", Microbiol. Mol. Biol. R v. 62:547–85 (1998).
Buckland, Barry, et al., "Production of Lovastatin, an Inhibitor of Cholesterol Accumulation in Humans", Topics in Industrial Microbiology: Novel Microbial Products for Medicine and Agriculture, pp. 161–169, Elsevier, Amsterdam (1989).
Bundgaard, H. et al., "A New Spectrophotometric Method for the Determination of Penicillins", *Journal of Pharm. Pharmac.* 24:790–794 (1972).

(Continued)

*Primary Examiner*—James Ketter
*Assistant Examiner*—David A. Lambertson
(74) *Attorney, Agent, or Firm*—Fish & Richardson P.C.

(57) ABSTRACT

The invention relates to the production of secondary metabolites by fungi. More particularly, the invention relates to improvement of production of commercially important secondary metabolites by fungi. The invention provides methods for improving secondary metabolite production in a fungus, comprising modulating the expression of a gene involved in regulation of secondary metabolite production.

50 Claims, 2 Drawing Sheets

OTHER PUBLICATIONS

Casquiero, Javier et al., "Gene Targeting in *Penicillium chrysogenum*: Disruption of the lys2 Gene Leads to Penicillin Overproduction", J. Bacteriol. 181:1181–1188 (1999).

Cardenas, Maria et al., "Targets of Immunophilin–immunouppressant Complexes are Distinct Highly Conserved Regions of Calcineurin A", EMBO J 14: 2772–83 (1995).

Chen, Yan et al., "Mapping Mutations in Genes Encoding the Two Large Subunits of *Drosophila* RNA Polymerase II Defines Domains Essential for Basic Transcription Functions and for Proper Expression of Developmental Genes", Mol. Cell. Biol. 13:4214–22 (1983)

Decottignies, Anabelle et al., "Complete Inventory of the Yeast ABC Proteins", Nat Genet. 15:137–45 (1997).

Demain, Arnold L., Microbial Secondary Metabolism: A New Theoretical Frontier for Academia, a New Opportunity for Industry:, Ciba Found Symp. 171:3–16 (1992).

Donald, K. Allen et al., "Effects of Overproduction of the Catalytic Domain of 3–Hydroxy–3–Methylgutaryl Coenzyme A Reductase on Squalene Synthesis in *Saccharomyces cerevisiae*", Appl. Environ. Microbiol. 63:3341–4 (1997).

Douglas, C.M. et al., "Identification of the FKS1 Gene *Candida albicans* as the Essential Target of 1,3–62–D–Glucan Synthase Inhibitors", Antimicrob. Agents Chemother. 41:2471–9 (1997).

Drgonova, Jana et al., "Rho1p, a Yeast Protein at the Interface Between Cell Polarization and Morphogenesis", Science 272:277–279 (1996).

Feller, Andre et al., "In *Saccharomyces cerevisae*, Feedback Inhibition of Homocitrate Synthase Isoenzymes by Lysine Modulates the Activation of LYS Gene Expression by Lys14p", Eur. J. Biochem. 261: 163–70 (1999).

Gonzalez–Garay, Manuel L. et al., "A β–Tubulin Leucine Cluster Involved in Microtubule Assembly and Paclitaxel Resistance", J. Biol. Chem. 274:23875–82 (1999).

Griffin, DH, ed. "Secondary (Special) Metabolism" Fungal Physiology, Ch. 9 pp. 246–274 ed. (1994).

Heinisch, Jurgen, J. et al., "The Protein Kinase C–mediated MAP Kinase Pathway Involved in the Maintenance of Cellular Integrity in *Saccharomyces cerevisiae*", Mol. Microbiol. 32:671–680 (1999).

Jensen, S.E. et al., "Beta–Lactams" Biotechnology 28:239–68 (1995).

Katzmann, David J. et al., "Transcriptional Control of the Yeast PDR5 Gene by the PDR3 Gene Product", Mol. Cell. Biol. 14:4653–61 (1994).

Kennedy, Jonathan et al., "Modulation of Polyketide Synthase Activity by Accessory Proteins During Lovastatin Biosynthesis", Science 284:1368–72 (1999).

Lowther, W. Todd et al., "The Anti–angiogenic Agent Fumagillin Covalently Modifies a Conserved Active–site Histidine in the *Escherichia coli* Methionine Aminopeptidase", Proc. Natl. Sci. USA 95:12153–7 (1998).

Luengo, Jose et al., "Penicillin Biosynthesis", Prog. Ind. Microbiol 29:603–38 (1994).

Lum, Pek Yee et al., "Molecular, Functional and Evolutionary Characterization of the Gene Encoding HMG–CoA Reductase in the Fission Yeast, *Schizosaccharomyces prombe*", Yeast 12:1107–24 (1996).

Mingot, Jose et al., "Disruption of phacA, an *Aspergillus nidulans* Gene Encoding a Novel Cytochrome P450 Monoxygenase Catalyzing Phenylacetate 2–Hydroxylation, Results in Penicillin Overproduction", J. Biol. Chem. 21:14545–14550 (1999).

Nakaune, Ryoji et al., "A Novel ATP–Binding Cassette Transporter Involved in Multidrug Resistance in the Phytopathogenic Fungus *Penicillium digitatum*", Appl. Environ. Microbiol. 64:3983–8 (1998).

Nelisssen, Bart et al., "Classification of All Putative Permeases and Other Membrane Plurispanners of the Major Facilitator Superfamily Encoded by the Complete Genome of *Saccharomyces cervisiae*", FEMS Microbiol. Rev. 21:113–34 (1997).

Nonaka, Hidetaro et al., "a Downstream Target of RHO1 Small GTP–binding Protein is PKC1, a Homolog of Protein Kinase C., Which Leads to Activation of the MAP Kinase Cascade in *Saccharomyces cerevisiae*", EMBO J. 14:5931–5938 (1995).

Norman, Thea C. et al., "Genetic Selection of Peptide Inhibitors of Biological Pathways", Science 285:591–595 (1999).

Oskouian, B. et al., "YAP1 Confers Resistance to the Fatty Acid Synthase Inhibitor Cerulenin Through the Transporter Flr1p in *Saccharomyces cerevisiae*", Mol. Gen. Genet. 261:346–53 (1999).

Penalva, Miguel A. et al., "The Optimization of Penicillin Biosynthesis in Fungi", Trends Biotechnol. 16:483–489 (1998).

Qadota, Hiroshi et al., "Identification of Yeast Rho1p GTPase as a Regulatory Subnit of 1,3–β–Glucan Synthase", Science 272:279–281 (1996).

Ravid, Tommer et al., "Imparied Regulation of 3–Hydroxy–3methylglutary–Coenzyme A Reductase Degradation in Lavastatin–resistant Cells", J. Biol. Chem. 274:29341–51 (1999).

Reid, Robert J.D. et al., "Camptothecin Sensitivity is Mediated by the Pleiotropic Drug Resistance Network in Yeast", J. Biol. Chem. 272:12091–9 (1997).

Sanglard, D. et al., "Mechanisms of Resistance to Azole Antifungal Agents in *Candida albicans* Isolates from AIDS Patients Involve Specific Multidrug Transporters", Antimicrob. Agents Chemother. 39:2378–86 (1995).

Seron, Karin et al., "Uracil–induced Down–regulation of the Yeast Uracil Permease", J. Bacteriol. 181: 1793–800 (1999).

Silar P., "Two New Easy to Use Vectors for Transformations", Fungal Genetics Newsletter 42:73 (1995).

Sin, Ny et al., "The Anti–angiogenic Agent Fumagillin Covalently Binds and Inhibits the Methionine Aminopeptidase, MetAP–2", Proc. Natl. Acad. Sci. USA 94:6099–103 (1997).

Wendler, Franz et al., "Diazaborine Resistance in the Yeast *Saccharomyces cerevisiae* Reveals a Link between YAP1 and the Pleiotropic Drug Resistance Genes PDR1 and PDR3", J. Biol. Chem. 272:27091–8 (1997).

Wolschek, Markus F. et al., "The Filamentous Fungus *Aspergillus niger* Contains Two "Differentially Regulated" Trehalose–6–phosphate Synthase–encoding Genes, tpsA and tpsB", J. Biol. Chem. 272:2729–2735 (1997).

Parekh et al. Applied Microbiology and Biotechnology 54:287–301 2000.*

* cited by examiner

METHODS FOR IMPROVING SECONDARY METABOLITE PRODUCTION IN FUNGI This application claims priority under 35 U.S.C. § 119(c) to U.S. provisional application No. 60/160,587, filed Oct. 20, 1999.

BACKGROUND OF THE INVENTION

1. Field of the Invention

The invention relates to the production of secondary metabolites by fungi. More particularly, the invention relates to improvement of production of commercially important secondary metabolites by fungi.

2. Summary of the Related Art

Secondary metabolite production by various fungi has been an extremely important source of a variety of therapeutically significant pharmaceuticals. B-lactam antibacterials such as penicillin and cephalosporin are produced by *Penicillium chrysogenum* and *Acremonium chrysogenum*, respectively, and these compounds are by far the most frequently used antibacterials (reviewed in Luengo and Penalva, Prog. Ind. Microbiol. 29: 603–38 (1994); Jensen and Demain, Biotechnology 28: 239–68 (1995); Brakhage, Microbiol. Mol. Biol. Rev. 62: 547–85 (1998)). Cyclosporin A, a member of a class of cyclic undecapeptides, is produced by *Tolypocladium inflatum*. Cyclosporin A dramatically reduces morbidity and increases survival rates in transplant patients (Borel, Prog. Allergy 38: 9–18 (1986)). In addition, several fungal secondary metabolites are cholesterol lowering drugs, including lovastatin that is made by *Aspergillus terreus* and several other fungi (Alberts et al., Proc. Natl. Acad. Sci. USA 77: 3957–3961 (1980)). These and many other fungal secondary metabolites have contributed greatly to health care throughout the world (see Demain, Ciba Found Symp 171: 3–16 (1992); Bentley, Crit. Rev. Biotechnol. 19: 1–40 (1999)).

Unfortunately, many challenges are encountered between the detection of a secondary metabolite activity to production of significant quantities of pure drug. Thus, efforts have been made to improve the production of secondary metabolites by fungi. Some of these efforts have attempted to improve production by modification of the growth medium or the bioreactor used to carry out the fermentation. Buckland et al., in Topics in Industrial Microbiology: Novel Microbial products for Medicine and Agriculture, pp. 161–169, Elsevier, Amsterdam (1989) discloses improved lovastatin production by modification of carbon source and also teaches the superiority of a hydrofoil axial flow impeller in the bioreactor. Other efforts have involved strain improvements, either through re-isolation or random mutagenesis. Agathos et al., J. Ind. Microbiol. 1: 39–48 (1986), teaches that strain improvement and process development together resulted in a ten-fold increase in cyclosporin A production. While important, studies of these types have still left much room for improvement in the production of secondary metabolites.

More recently, strains have been improved by manipulation of the genes encoding the biosynthetic enzymes that catalyze the reactions required for production of secondary metabolites. Penalva et al., Trends Biotechnol. 16: 483–489 (1998) discloses that production strains of *P. chrysogenum* have increased copy number of the penicillin synthesis structural genes. Other studies have modulated expression of other biosynthetic enzyme-encoding genes, thereby affecting overall metabolism in the fungus. Mingo et al., J. Biol. Chem. 21: 14545–14550 (1999), demonstrate that disruption of phacA, a gene required for phenylacetate catabolism in *A. nidulans*, leads to increased penicillin production, probably by allowing increased availability of phenylacetate for secondary metabolism. Similarly, disruption of the gene encoding aminoadipate reductase in *P. chrysogenum* increased penicillin production, presumably by eliminating competition for the substrate alpha-aminoadipate (Casquiero et al., J. Bacteriol. 181: 1181–1188 (1999)).

Thus, genetic manipulation holds promise for improving production of secondary metabolites. Genetic manipulation to increase the activity of biosynthetic enzymes for secondary metabolite production or to decrease the activity of competing biosynthetic pathways has proven effective for improving production. Maximum benefit might be achieved by combining several strategies of manipulation. For example, modulating the expression of genes that regulate the biosynthetic enzyme-encoding genes might improve production. In addition, genetic manipulation could be used to impact upon the challenges that are encountered in the fermentor run or downstream processing (e.g. energy cost, specific production of desired metabolite, maximal recovery of metabolite, cost of processing waste from fermentations). There is, therefore, a need for methods for improving secondary metabolite production in a fungus, comprising modulating the expression of a gene involved in regulation of secondary metabolite production. Ideally, such methods should be able to provide a means to modulate parameters important in production of secondary metabolites, including, yield, productivity, efflux/excretion, production of side products or non-desired secondary metabolites, strain characteristics such as morphology, conditional lysis, or resistance to the deleterious effects of exposure to a secondary metabolite.

BRIEF SUMMARY OF THE INVENTION

The invention provides methods for improving secondary metabolite production in a fungus, comprising modulating the expression of a gene involved in regulation of secondary metabolite production. The methods according to the invention provide increased yield, increased productivity, increased efflux/excretion, decreased production of side products or non-desired secondary metabolites, altered strain characteristics and/or conditional lysis, or increased resistance to the deleterious effects of exposure to a secondary metabolite.

The several aspects of the methods according to the invention are preferably achieved by overexpression of regulatory genes, expression of dominant mutant variants of regulatory genes, use of peptide activators or inhibitors of regulatory gene function, use of small molecule activators or inhibitors of regulatory gene function, and conditional expression of regulatory genes. These factors preferably are or modulate transcription factors, transmembrane transporters, proteins that mediate secretion, kinases, G-proteins, cell surface receptors, GTPase activating proteins, guanine nucleotide exchange factors, phosphatases, proteases, phosphodiesterases, bacterial protein toxins, importins, RNA-binding proteins, SCF complex components, adherins, or biosynthetic pathways.

The invention further provides for achieving the aspects described in the invention by combinatorial manipulation. Combinatorial manipulation is the simultaneous use of multiple methods and/or multiple factors to achieve the aspects of the invention. Methods for achieving the aspects of the invention are preferably by the overexpression of regulatory genes, expression of dominant mutant variants of regulatory genes, use of peptide activators or inhibitors, use of small molecule activators or inhibitors, and conditional expression of regulatory genes. The preferred factors are as described above.

The invention further provides genetically modified fungi, wherein the genetically modified fungi have an ability to produce secondary metabolites and the ability of the genetically modified fungus to produce secondary metabolites has been improved by any of the methods according to the invention.

The invention also provides a method for making a secondary metabolite, the method comprising culturing a genetically modified fungus according to the invention under conditions suitable for the production of secondary metabolites.

DETAILED DESCRIPTION OF THE PREFERRED EMBODIMENTS

Figure 1:
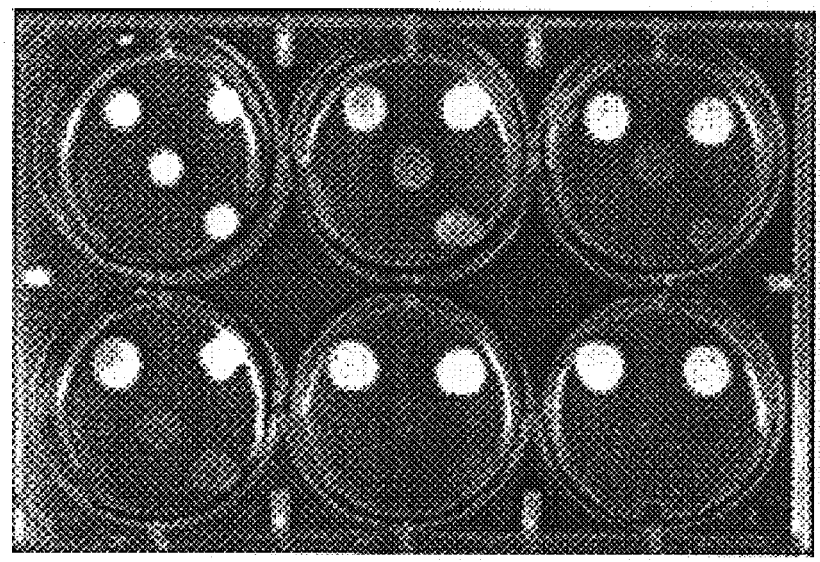
FIG. 1 shows the ability of PUMP1 (AAD34558) from *Aspergillus terreus* to confer lovastatin resistance to a yeast strain.
Figure 1:
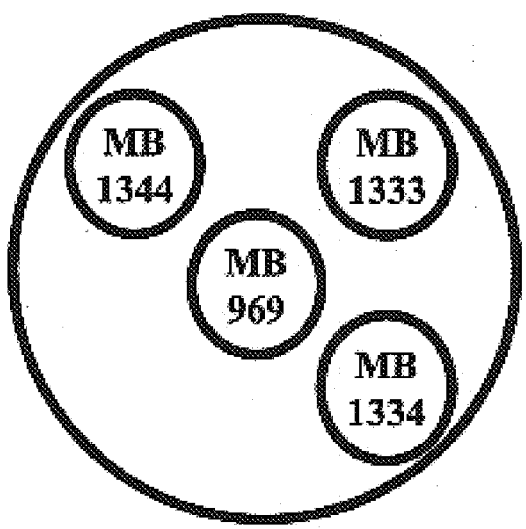
Figure 2:
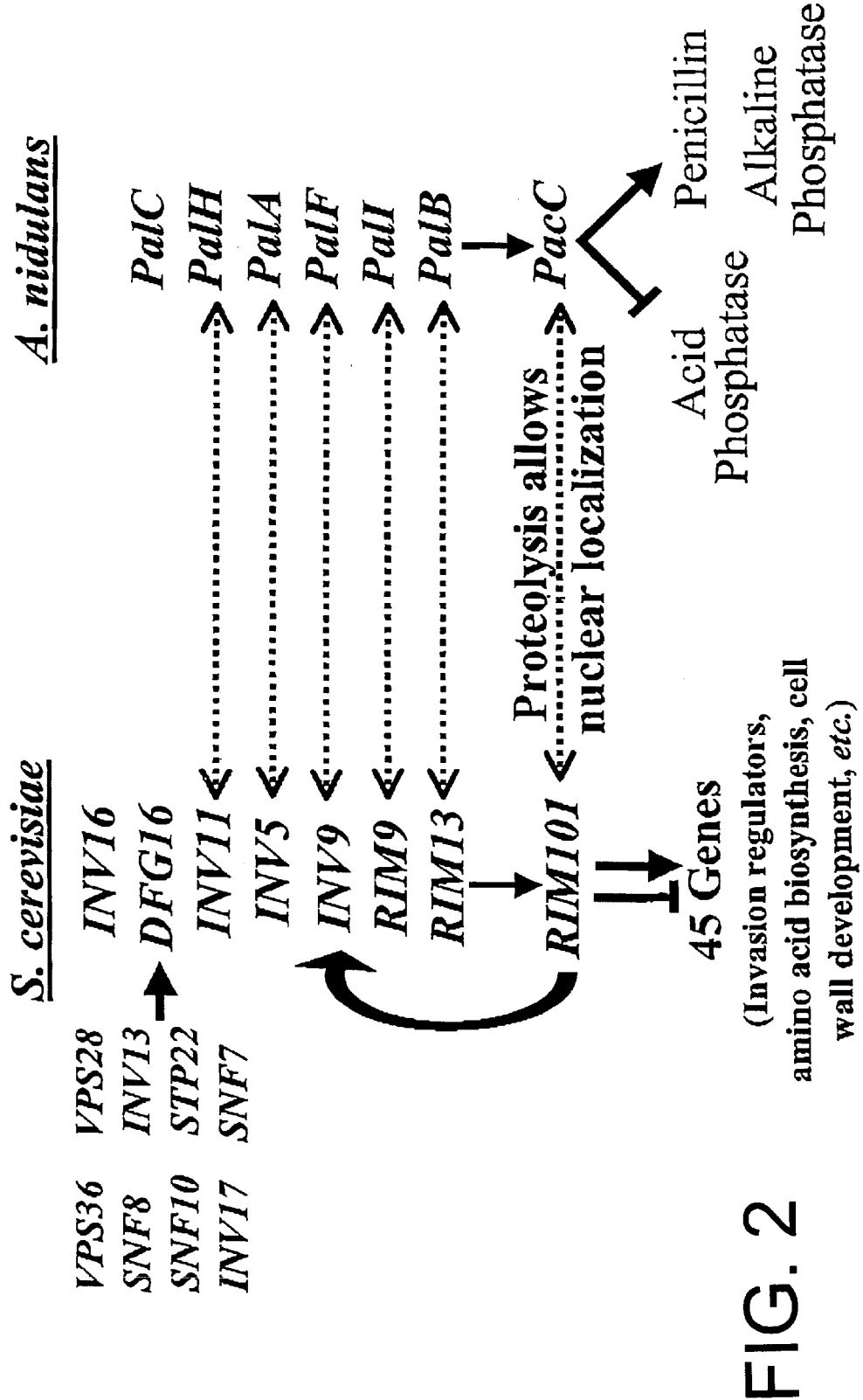
FIG. 2 shows that a yeast genetics and genomics can provide insight into mechanisms for production of secondary metabolites. Arrows indicate which genes or gene products act on other genes or gene products, and dotted lines indicate homologous proteins. This figure demonstrates that yeast proteins that regulate the yeast invasion response have homologues in filamentous fungi that regulate the production of secondary metabolites, such as penicillin. Furthermore, the genomic tools and molecular genetics of *Saccharomyces cerevisiae* may facilitate the understanding of pathways that regulate secondary metabolism in other fungi.

The invention relates to the production of secondary metabolites by fungi. More particularly, the invention relates to improvement of production of commercially important secondary metabolites by fungi. The references cited herein evidence the level of knowledge in the field and are therefore incorporated by reference in their entirety. In the event of a conflict between a cited reference and the present specification, the latter shall prevail.

The invention provides methods for improving secondary metabolite production in a fungus, comprising modulating the expression of a gene involved in regulation of secondary metabolite production. In certain embodiments, the methods comprise modulating the expression of more than one gene involved in regulation of secondary metabolite production.

In a first aspect, the invention provides methods for improving production of a secondary metabolite by a fungus by increasing the yield of the secondary metabolite produced by the fungus. The methods according to this aspect of the invention comprise modulating the expression of a gene involved in regulation of secondary metabolite production in a manner that improves the yield of the secondary metabolite.

Preferably, for this aspect of the invention, when the secondary metabolite is isopenicillin N, then the modulation is not mediated by the transcription factor CPCR1; when the secondary metabolite is sterigmatocystin, then the modulation is not through AflR, FadA, or FluG; when the secondary metabolite is aflatoxin, then the modulation is not through AflR; when the secondary metabolite is penicillin and the fungus is *Aspergillus nidulans*, then the modulation is not through mutations that result in expression of truncated forms of PacC or constitutively active forms of FadA; when the gene involved in regulation of secondary metabolite production is from *Saccharomyces cerevisiae*, then the modulation is not through decreased activity or expression of Bem2, Hog1, Ira1, Rim15, Sfl1, Srb11, Ssd1, Swi4, Tpk3 or though increased activity or expression of Afl1, Cdc25, Dhh1, Hap4, Inv11, Inv13, Inv5, Inv7, Inv9, Mcm1, Mep2, Mga1, Msn1, Msn5, Mss11, Pet9, Pho23, Ptc1, Rim101, Rim13, Rim9, Snf8, Stp22, Tpk2, Vps28, Vps36, or Ypr1.

As used for all aspects of the invention, the term "improving production of a secondary metabolite" means to positively impact upon one or more of the variables that affect the process of production of secondary metabolites in a fungal fermentation. These variables include, without limitation, amount of secondary metabolite being produced, the volume required for production of sufficient quantities, the cost of raw materials and energy, the time of fermentor run, the amount of waste that must be processed after a fermentor run, the specific production of the desired metabolite (both in total amounts and as a fraction of all secondary metabolites and side products made by the fungus), the percent of produced secondary metabolite that can be recovered from the fermentation broth, and the resistance of an organism producing a secondary metabolite to possible deleterious effects of contact with the secondary metabolite. Also for all aspects, the term "secondary metabolite" means a compound, derived from primary metabolites, that is produced by an organism, is not a primary metabolite, is not ethanol or a fusel alcohol, and is not required for growth under standard conditions. Secondary metabolites are derived from intermediates of many pathways of primary metabolism. These pathways include, without limitation, pathways for biosynthesis of amino acids, the shikimic acid pathway for biosynthesis of aromatic amino acids, the polyketide biosynthetic pathway from acetyl coenzyme A (CoA), the mevalonic acid pathway from acetyl CoA, and pathways for biosynthesis of polysaccharides and peptidopolysaccharides. Collectively, secondary metabolism involves all primary pathways of carbon metabolism (*Fungal Physiology*, Chapter 9 pp 246–274 ed D H Griffin (1994)). "Secondary metabolites" also include intermediate compounds in the biosynthetic pathway for a secondary metabolite that are dedicated to the pathway for synthesis of the secondary metabolite. "Dedicated to the pathway for synthesis of the secondary metabolite" means that once the intermediate is synthesized by the cell, the cell will not convert the intermediate to a primary metabolite. "Intermediate compounds" also include secondary metabolite intermediate compounds which can be converted to useful compounds by subsequent chemical conversion or subsequent biotransformation. As such, providing improved availability of such intermediate compounds would still lead to improved production of the ultimate useful compound, which itself may be referred to herein as a secondary metabolite. The yeast *Saccharomyces cerevisiae* is not known to produce secondary metabolites. The term "primary metabolite" means a natural product that has an obvious role in the functioning of almost all organisms. Primary metabolites include, without limitation, compounds involved in the biosynthesis of lipids, carbohydrates, proteins, and nucleic acids. The term "increasing the yield of the secondary metabolite" means increasing the quantity of the secondary metabolite present in the total fermentation broth per unit volume of fermentation broth.

A "gene involved in regulation of secondary metabolite production" is a gene, other than a gene encoding a biosynthetic enzyme for the secondary metabolite to be produced, which modulates secondary metabolite production involving yield, productivity, efflux/excretion, production of side products or non-desired secondary metabolites, strain characteristics and/or conditional lysis, or resistance to the deleterious effects of exposure to a secondary metabolite. A "biosynthetic enzyme for the secondary metabolite to be produced" is a molecule that catalyzes the conversion of a substrate to a product, including an intermediate product, in the biosynthetic pathway for the secondary metabolite for which production is being improved. An alternative term, "biosynthetic enzyme", as used herein refers to a molecule that catalyzes the conversion of a substrate to a product, including an intermediate product, in a biosynthetic pathway other than the biosynthetic pathway for the secondary metabolite for which production is being improved.

As used for all aspects of the invention, the term "modulating the expression of a gene" means affecting the function of a gene's product, preferably by increasing or decreasing protein activity through mutation, creating a new protein activity through mutation; increasing or decreasing transcription, increasing or decreasing translation, increasing or decreasing post-translational modification, altering intracellular localization, increasing or decreasing translocation from one cellular location to another, increasing or decreasing protein activity by interaction of the protein with another molecule, or creating a new protein activity by interaction of the protein with another molecule. In some cases, such modulation is achieved simply by allowing or causing the expression of an exogenously supplied nucleic acid or gene. In some cases other exogenously supplied molecules may mediate the modulation. The modulation is not achieved, however, by simply randomly mutagenizing the fungus, either spontaneously or by chemical means.

As used for all aspects of the invention, "mutation" means an alteration in DNA sequence, either by site-directed or random mutagenesis. Mutation encompasses point mutations as well as insertions, deletions, or rearrangements.

As used for all aspects of the invention, "mutant" means an organism containing one or more mutations.

In certain embodiments of the methods according to this aspect of the invention, the modulation is overexpression of the gene. "Overexpression of the gene" means transcription and/or translation and/or gene product maturation at a rate that exceeds by at least two-fold, preferably at least five-fold, and more preferably at least ten-fold, the level of such expression that would be present under similar growth conditions in the absence of the modulation of expression of the gene. In instances where heterologous genes are being expressed, any level of expression is, by definition, considered overexpression. "Similar growth conditions" means similar sources of nutrients such as carbon, nitrogen, and phosphate, as well as similar pH, partial oxygen pressure, temperature, concentration of drugs or other small molecules, and a similar substrate for growth, whether solid, semi-solid, or liquid. Preferred genes according to this aspect of the invention include, without limitation, AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes.

In certain embodiments of the methods according to this aspect of the invention, the modulation is expression of a dominant mutation of the gene. A "dominant mutation" is an allele of a gene that encodes a protein capable of changing the phenotype of an organism more than a non-mutated form of the gene. Dominant mutations include, without limitation, mutations that encode a protein capable of changing the phenotype of an organism even when a non-mutant form of this gene (or its homologs) is resident in the organism. Preferred dominant mutations include dominant negative mutations, dominant positive mutations, and dominant neomorphic mutations. A "dominant negative mutation" is a dominant mutation that achieves its phenotypic effect by interfering with some function of the gene or gene product from which it was derived, or from a homolog thereof. A "dominant positive mutation" is a dominant mutation that achieves its phenotypic effect by activating some function of the gene or gene product from which it was derived, or from a homolog thereof. A "dominant neomorphic mutation" is a dominant mutation that achieves the phenotypic effect of providing a novel function to the gene or gene product from which it was derived, or from a homolog thereof. Preferred dominant mutations according to this aspect of the invention include:

1. Mutations that result in increased or decreased stability of the transcript of a gene.
2. Mutations that result in increased or decreased stability of the product of translation: For example, specific sequences near the amino terminus of a protein have been shown to cause increased or decreased protein stability. Similarly, sequences elsewhere in the protein, such as those required for ubiquitin-dependent degradation, can be mutated to increase the stability of a protein.
3. Amino acid substitutions that mimic post-translational modifications: For example, phosphorylation has been demonstrated to positively or negatively regulate the activity of a variety of proteins, including transcription factors and kinases. Phosphorylation most commonly occurs on serine, threonine, and tyrosine residues; in some instances residues such as aspartate and histidine can be phosphorylated. Mutations that mimic constitutive dephosphorylation can be produced by mutating the coding sequence of the phosphorylated residue to the coding sequence of an amino acid that cannot be phosphorylated and does not have a negatively charged side chain (e.g. alanine). Alternatively, substitutions that result in changing serine, threonine, or tyrosine residues to charged amino acids such as glutamate or aspartate can result in an allele that mimics constitutive phosphorylation.

Proteolytic cleavage is another post-translational mechanism for regulating the activity of a protein. Mutations that result in truncation of a protein might mimic activation by proteolysis. Mutations that change amino acids required for proteolysis could activate proteins that are negatively regulated by proteolysis.

4. Amino acid substitutions that promote or inhibit the binding of small molecules such as ATP, cAMP, GTP or GDP: For example, ATP is a co-factor for many enzymatic reactions, and the nucleotide-binding domains of these proteins are highly conserved. Lysine to arginine substitutions in the nucleotide-binding domain frequently result in inhibition of enzymatic activity. Enzymatically inactive proteins could be dominant negative molecules, acting by sequestering substrates from functional enzymes.

cAMP is required for the activation of protein kinase A. Protein kinase A consists of regulatory subunits and catalytic subunits. The binding of cAMP to the negative regulatory subunit relieves its inhibition of the catalytic subunit. Therefore, mutations that prevent cAMP binding could result in constitutive inactivation of protein kinase A.

G-proteins are a class of proteins that bind the nucleotides GTP and GDP. The GTP-bound form of these proteins is active, and hydrolysis of GTP to GDP results in the inactivation of the protein. Conserved substitutions can be made to lock G-proteins in either the GTP- or GDP-bound form, thus causing constitutive activation or inactivation.

5. Mutations in portions of genes that encode regulatory domains of proteins: For example, many proteins, including kinases, contain regulatory domains that function as mechanisms to control the timing of activation. Mutations in these domains might result in constitutive activation of the kinase. Mutations that result in increased binding to regulatory proteins might result in constitutive inactivation.

Regulatory domains include short peptide sequences such as those required for nuclear import or export. Mutations in these sequences would result in constitutive cytoplasmic or nuclear localization, respectively, which could either activate or inhibit signaling.

6. Mutations that result in proteins that are capable of binding to an appropriate signaling partner, but the complexes that form are inactive: For example, dimerization of proteins, either homodimers or heterodimers, often is required for signaling; in many instances, short protein sequences are sufficient to promote dimerization. Mutations in functional domains not required for dimerization might result in dominant inhibition; these proteins are capable of binding to and possibly sequestering other signaling molecules into inactive, or partially inactive, complexes.

7. Mutations that decrease or increase the targeting of proteins to the appropriate subcellular destination: Short peptide sequences often facilitate the targeting of proteins to specific subcellular locations. For example, short sequences are sufficient to be recognized and modified by fatty acylation, prenylation, or glycosylphosphatidylinositol modification. These modifications result in targeting of proteins to membranes. Membrane spanning peptide sequences also have been identified, as have targeting sequences for secretion. In addition, sequences have been identified that target proteins to subcellular locations such as the endoplasmic reticulum, mitochondria, peroxisome, vacuole, nucleus, and lysosome. Mutations that inhibit proper targeting might result in dominant inhibition; these proteins might be capable of binding to and possibly sequestering other signaling molecules from the appropriate subcellular location.

8. Mutations that create a new protein function. For example, a mutation in a protein kinase could result in altered substrate specificity, such that the mutated kinase can modulate the activity of pathways that it does not usually regulate.

In certain embodiments of the methods according to this aspect of the invention, the modulation is mediated by a peptide modulator of gene expression. The term "peptide" means a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), chelation, electrostatic interactions, hydrophobic interactions, hydrogen bonding, ion-dipole interactions, dipole-dipole interactions, or any combination of the above. Peptides may be expressed in the cell or supplied exogenously. Preferably, they are provided on a scaffold to increase intracellular stability and to provide conformational constraint. A "scaffold" is a molecule, most frequently a small protein, from which a peptide is displayed; scaffolds are employed to optimize presentation, rigidity, conformational constraint, and potentially intracellular/extracellular localization. Preferred scaffolds include a catalytically inactive version of staphylococcal nuclease. Preferred peptides according to this aspect of the invention include, without limitation, those peptides disclosed in Norman et al., Science 285: 591–595 (1999).

In certain embodiments of the methods according to this aspect of the invention, the peptide modulator is an activator of gene expression. An "activator of gene expression" is a molecule that causes transcription and/or translation and/or gene product maturation to exceed by at least two-fold, preferably at least five fold, and more preferably at least ten-fold, the level of such expression that would be present under similar growth conditions in the absence of the activator of expression of the gene. "Similar growth conditions" is as used before.

In certain embodiments of the methods according to this aspect of the invention, the peptide modulator is an inhibitor of gene expression. An "inhibitor of gene expression" is a molecule that causes transcription and/or translation and/or gene product maturation to be reduced by at least two-fold, preferably at least five fold, and more preferably at least ten-fold, the level of such expression that would be present under similar growth conditions in the absence of the inhibitor of expression of the gene. "Similar growth conditions" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before. A "small molecule" is a compound with a preferable molecular weight below 1000 daltons.

In certain embodiments of the methods according to this aspect of the invention, the modulation is conditional expression of the gene. "Conditional expression" of a gene means expression under certain growth conditions, but not under others. Such growth conditions that may be varied include, without limitation, carbon source, nitrogen source, phosphate source, pH, temperature, partial oxygen pressure, the presence or absence of small molecules such as drugs, and the presence or absence of a solid substrate.

In certain embodiments of the methods according to this aspect of the invention, the gene either encodes a transcription factor or the product that it encodes acts on a transcription factor. As used throughout this specification, the term "the gene acts on" means that the gene or its transcriptional, translational, or post-translationally modified product affects the function of its target (for the remainder of the text, the target is the word or phrase that follows the expression "the gene acts on"), preferably by increasing or decreasing transcription, increasing or decreasing translation, increasing or decreasing post-translational modification, increasing or decreasing protein stability, increasing or decreasing protein translocation, or increasing or decreasing protein function by interaction of the protein with another molecule. A "transcription factor" is a molecule that activates or inhibits transcription. The term "activates transcription" means to cause transcription to exceed by at least two-fold, preferably at least five-fold, and more preferably at least ten-fold, the level of transcription that would be present under similar growth conditions in the absence of the transcription factor. The term "inhibits transcription" means to cause transcription to be reduced by at least two-fold, preferably at least five-fold, and more preferably at least ten-fold, the level of such transcription that would be present under similar growth conditions in the absence of the transcription factor. Preferred transcription factors include, without limitation, transcription factors that modulate the expression of genes involved in the production or response to the small molecule cAMP (preferred examples include, without limitation, Mga1, Msn2, Msn4, Sfl1, and Sok2); transcription factors that function downstream of mitogen-activated protein (MAP) kinase signaling pathways that regulate the yeast invasion response (preferred examples include, without limitation, Mcm1, Ste12, and Tec1); transcription factors that modulate the expression of genes involved in nitrogen regulation (preferred examples include, without limitation, AreA, Gln3, Hms1, Hms2, NreB, TamA, and Uga3); transcription factors that modulate the expression of genes involved in pH regulation in fungi (preferred examples include, without limitation PacC and Rim101); general transcription factors (preferred examples include, without limitation, Sin3, Snf2, Srb8, Srb9, Srb10, Srb11, Ssn6, and Tup1); transcription factors that modulate the expression of genes involved in carbon metabolism (preferred examples include, without limitation, Adr1, Cat8, CreA, FacB, Gcr1, Gcr2, Hap4, Mig1, Mig2, Mth1, Nrg1, Oaf1, and Sip4); heme-dependent transcription factors (preferred examples include, without limitation, Hap1 and Rox1); transcription factors that modulate the expression of genes involved in the uptake of metals (preferred examples include, without limitation, Aft1, Cup9, Mac1, SreP, SreA, and Zap1); transcription factors that modulate the expression of genes involved in cell-cycle regulation (preferred examples include, without limitation, Skn7, Swi4, and Swi6); transcription factors that modulate the expression of genes involved in invasion (preferred examples include, without limitation, Ash1, Flo8, Gts1, Inv7, Msn1, Mss11, Phd1, and Rre1); transcription factors that modulate the expression of genes involved in amino acid biosynthesis or transport (preferred examples include, without limitation, Gcn4, Leu3, Lys14, Met4, Met28, Met31, MetR, Put3, SconB, and Uga3); transcription factors that modulate the expression of genes involved in phosphate metabolism or transport (preferred examples include, without limitation, Pho2 and Pho4); transcription factors that modulate the expression of genes involved in nucleotide metabolism or transport (preferred examples include, without limitation, Ppr1 and UaY); transcription factors that modulate the expression of genes involved in cell wall processes (preferred examples include, without limitation, Ace2, Swi4, and Swi6); transcription factors that modulate the expression of genes involved in sporulation (preferred examples include, without limitation, Ime1 and Ime4); transcription factors that modulate the expression of genes involved in phospholipid synthesis (preferred examples include, without limitation, Ino2); transcription factors that modulate the expression of genes involved in aflatoxin biosynthesis (preferred examples include, without limitation, AflR); transcription factors that modulate the expression of genes involved in lovastatin biosynthesis (preferred examples include, without limitation, AAD34561 and LovE); and transcription factors that modulate the expression of genes involved in filamentous fungal development (preferred examples include, without limitation, AbaA). The term "general transcription factors" means components involved in the formation of preinitiation complexes at promoters that are regulated by RNA polymerase II. The term "invasion" means a process by which a fungus penetrates, digs, adheres to, or attaches to a substrate.

In certain embodiments of the methods according to this aspect of the invention, the gene either encodes a transmembrane transporter or the product that it encodes acts on a transmembrane transporter. A "transmembrane transporter" is a molecule or complex of molecules that facilitates passage of another type of molecule from one side of a cellular membrane to the other side in an energy-dependent or energy-independent manner. "Facilitates passage" means that the number of molecules traversing the membrane is greater than it would have been in the absence of the transmembrane transporter, preferably at least two-fold greater, more preferably at least ten-fold greater, even more preferably at least one hundred-fold greater, and most preferably at least one thousand-fold greater. Preferred classes of transmembrane transporters include, without limitation, proteins of the ATP-binding cassette superfamily, members of the Major Facilitator Superfamily (MFS) that include, without limitation Pump1 and Pump2, P-type ATPases, members of the mitochondrial carrier family (MCF) that include, without limitation, Pet9 and AAD34562, ion channels, permeases that include, without limitation, Bap2, Hip1, Mep1, and Mep2; and components that transport sugars, ions, or metals.

In certain embodiments of the methods according to this aspect of the invention, the gene either encodes a kinase or the product that it encodes acts on a kinase. A "kinase" is a molecule that phosphorylates a protein, a lipid, a nucleic acid, a carbohydrate, or any other substrate that is capable of being phosphorylated. Preferred kinases include, without limitation, Cdc28, Elm1, Fus3, Gcn2, Hog1, Hsl1, Hxk2, Kss1, Pbs2, Pho85, Rim15, Ste7, Sch9, Snf1, Ste11, Ste20, Tpk1, Tpk2, and Tpk3.

In certain embodiments of the methods according to this aspect of the invention, the gene either encodes a G-protein or the product that it encodes acts on a G-protein. A "G-protein" is a guanyl-nucleotide binding protein. Preferred G-proteins include, without limitation Cdc42, FadA, Gpa1, Gpa2, Ras1, and Ras2.

In certain embodiments of the methods according to this aspect of the invention, the gene either encodes a cell surface receptor or the product that it encodes acts on a cell surface receptor. A "cell surface receptor" is a molecule that resides at the plasma membrane, binds an extracellular signaling molecule, and transduces this signal to propagate a cellular response. Preferred cell surface receptors include, without limitation, G-protein coupled receptors. Preferred G-protein coupled receptors include, without limitation, Gpr1.

In certain embodiments of the methods according to this aspect of the invention, the gene either encodes a GTPase activating protein or the product that it encodes acts on a GTPase activating protein. A "GTPase activating protein" is a molecule that promotes the hydrolysis of GTP bound to a G-protein. GTP-activating proteins often negatively regulate the activity of G-proteins. Preferred GTPase activating proteins include, without limitation, RGS family members. "RGS family members" are regulators of G-protein signaling that act upon G-protein coupled receptors. Preferred RGS family members include, without limitation, FlbA, Rgs2, and Sst2.

In certain embodiments of the methods according to this aspect of the invention, the gene either encodes a guanine nucleotide exchange factor or the product that it encodes acts on a guanine nucleotide exchange factor. A "guanine nucleotide exchange factor" is a molecule that catalyzes the dissociation of GDP from the inactive GTP-binding proteins; following dissociation, GTP can then bind and induce structural changes that activate G-protein signaling. Preferred guanine nucleotide exchange factors include, without limitation, Cdc24 and Cdc25.

In certain embodiments of the methods according to this aspect of the invention, the gene either encodes a phosphatase or the product that it encodes acts on a phosphatase. A "phosphatase" is a molecule that dephosphorylates a protein, a lipid, a nucleic acid, a carbohydrate, or any other substrate that is capable of being dephosphorylated. Preferred phosphatases include, without limitation, Cdc55 and Ptc1.

In certain embodiments of the methods according to this aspect of the invention, the gene either encodes a protease or the product that it encodes acts on a protease. A "protease" is a molecule that cleaves one or more amide bonds in a peptide or protein. "Peptide" is as used before. Preferred proteases include, without limitation, Rim13 and LF.

In certain embodiments of the methods according to this aspect of the invention, the gene either encodes a cyclic nucleotide phosphodiesterase or the product that it encodes acts on a cyclic nucleotide phosphodiesterase. A "cyclic nucleotide phosphodiesterase" is a molecule that catalyzes the hydrolysis of the 3' phosphate bond of a 3', 5' cyclic nucleotide to yield free 5' nucleotide. Preferred examples of cyclic nucleotide phosphodiesterases include, without limitation, Pde2.

In certain embodiments of the methods according to this aspect of the invention, the gene either encodes a bacterial protein toxin or the product that it encodes acts on a bacterial protein toxin. A "bacterial protein toxin" is protein produced by a bacterium, as part of the pathogenesis of the bacterial organism, to kill or impair the biological function of the host organism. Bacterial protein toxins exhibit a wide-variety of biochemical and enzymatic activities including those of adenylate cyclases, ADP-ribosyltransferases, phospholipases, and proteases. Expression of bacterial protein toxins in fungi could result in increased production of secondary metabolites. Preferred bacterial protein toxins include, without limitation, Anthrax toxin edema factor (EF; *Bacillus anthracis*), Anthrax toxin lethal factor (LF; *Bacillus anthracis*), adenylate cyclase toxin (*Bordetella pertussis*), Cholera enterotoxin (*Vibrio cholerae*), LT toxin (*Escherichia coli*), ST toxin (*E. coli*), Shiga toxin (*Shigella dysenteriae*), Perfringens enterotoxin (*Clostridium perfringens*), Botulinum toxin (*Clostridium botulinum*), Tetanus toxin (*Clostridium tetani*), Diphtheria toxin (*Corynebacterium diphtheriae*), Exotoxin A (*Pseudomonas aeruginosa*), Exoenzyme S (*P. aeruginosa*), Pertussis toxin (*Bordetella pertussis*), alpha and epsilon toxins (*C. perfringens*), lethal toxin (LT; *Clostridium sordellii*), toxins A and B (*Clostridium dificile*), and phospholipase C (*Clostridium bifermentans*).

In certain embodiments of the methods according to this aspect of the invention, the gene either encodes an importin protein or the product that it encodes acts on an importin protein. An "importin" protein is a molecule that functions in the translocation of proteins from the nucleus to the cytosol or from the cytosol to the nucleus. Preferred examples of importin proteins include, without limitation, Msn5.

In certain embodiments of the methods according to this aspect of the invention, the gene either encodes a RNA-binding protein or the product that it encodes acts on a RNA-binding protein. Preferred examples of RNA-binding proteins include, without limitation, Dhh1 and Whi3.

In certain embodiments of the methods according to this aspect of the invention, the gene either encodes a component of a SCF complex or the product that it encodes acts on a component of a SCF complex. A "component of a SCF complex" is a molecule in a multi-protein aggregate that targets various substrates involved in the G1 to S phase cell cycle transition for ubiquitin-dependent degradation. Preferred examples of components of a SCF complex include, without limitation, Grr1.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. An "anti-bacterial" is a molecule that has cytocidal or cytostatic activity against some or all bacteria. Preferred anti-bacterials include, without limitation, β-lactams. Preferred β-lactams include, without limitation, penicillins and cephalosporins and biosynthetic intermediates thereof. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is a drug administered to a patient diagnosed with elevated cholesterol levels, for the purpose of lowering the cholesterol levels. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is a molecule that reduces or eliminates an immune response in a host when the host is challenged with an immunogenic molecule, including immunogenic molecules present on transplanted organs, tissues or cells. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. An "ergot alkaloid" is a member of a large family of alkaloid compounds that are most often produced in the sclerotia of fungi of the genus *Claviceps*. An "alkaloid" is a small molecule that contains nitrogen and has basic pH characteristics. The classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. An "angiogenesis inhibitor" is a molecule that decreases or prevents the formation of new blood vessels. Angiogenesis inhibitors have proven effective in the treatment of several human diseases including, without limitation, cancer, rheumatoid arthritis, and diabetic retinopathy. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. A "glucan synthase inhibitor" is a molecule that decreases or inhibits the production of 1,3-β-D-glucan, a structural polymer of fungal cell walls. Glucan synthase inhibitors are a class of antifungal agents. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The "gliotoxin family of compounds" are related molecules of the epipolythiodioxopiperazine class. Gliotoxins display diverse biological activities, including, without limitation, antimicrobial, antifungal, antiviral, and immunomodulating activities. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. A "fungal toxin" is a compound that causes a pathological condition in a host, either plant or animal. Fungal toxins could be mycotoxins present in food products, toxins produced by phytopathogens, toxins from poisonous mushrooms, or toxins produced by zoopathogens. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Modulators of cell surface receptor signaling might function by one of several mechanisms including, without limitation, acting as agonists or antagonists, sequestering a molecule that interacts with a receptor such as a ligand, or stabilizing the interaction of a receptor and molecule with which it interacts. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. A "plant growth regulator" is a molecule that controls growth and development of a plant by affecting processes that include, without limitation, division, elongation, and differentiation of cells. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. A "pigment" is a substance that imparts a characteristic color. Preferred pigments include, without limitation, melanins and carotenoids.

In certain embodiments of the methods according to this aspect of the invention, the secondary metabolite is an insecticide or a biosynthetic intermediate thereof. An "insecticide" is a molecule that is toxic to insects. Preferred insecticides include, without limitation, nodulisporic acid.

In certain embodiments of the methods according to this aspect of the invention, the secondary metabolite is an anti-neoplastic compound or a biosynthetic intermediate thereof. An "anti-neoplastic" compound is a molecule that prevents or reduces tumor formation. Preferred anti-neoplastic compounds include, without limitation, taxol (paclitaxel) and related taxoids.

In certain embodiments of the methods according to this aspect of the invention, the gene is not AFL1, BEM2, CDC25, DHH1, HOG1, INV11, INV13, INV5, INV7, INV9, IRA1, MCM1, MEP2, MGA1, MSN1, MSN5, MSS11, PET9, PHO23, PTC1, RIM101, RIM13, RIM15, RIM9, SFL1, SNF8, SRB11, SSD1, STP22, SWI4, TPK2, TPK3, VPS28, VPS36, or YPR1. Each of these genes is as described in PCT Publication No. WO99/25865A1.

In certain embodiments of the methods according to this aspect of the invention, the gene is selected from the group consisting of AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes. A "fungal homolog" of a gene is a gene encoding a gene product that is capable of performing at least a portion of the function of the product encoded by the reference gene, and is substantially identical to the reference gene and/or the encoded product. "Substantially identical" means a polypeptide or nucleic acid exhibiting at least 25%, preferably 50%, more preferably 80%, and most preferably 90%, or even 95% identity to a reference amino acid sequence or nucleic acid sequence. For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison Wis. 53705, BLAST, BEAUTY, or PILEUP/PRETTYBOX programs). Most preferably, BLAST is used. Such software matches identical or similar sequences by assigning degrees of homology to various substitutions, deletions, and/or other modifications. Conservative substitutions typically include substitutions within the following group: glycine, alanine, valine, isoleucine, leucine; aspartic acid, glutamic acid, asparagine, glutamine; serine, threonine; lysine, arginine; and phenylalanine, tyrosine.

In certain embodiments of the methods according to this aspect of the invention, the methods further comprise purifying the secondary metabolite from a culture of the fungus. "Purifying" means obtaining the secondary metabolite in substantially pure form. "Substantially pure" means comprising at least 90%, more preferably at least 95%, and most preferably at least 99%, of the purified composition on a weight basis.

In a second aspect, the invention provides methods for improving production of a secondary metabolite by a fungus by increasing productivity of the secondary metabolite in the fungus, the methods comprising modulating the expression of a gene involved in regulation of secondary metabolite production in a manner that improves the productivity of the secondary metabolite. "Increasing productivity" means to increase the quotient for the equation: concentration of secondary metabolite divided by the product of time of fermentor run, fermentation volume, and grams of dry cell weight of biomass (Productivity=concentration metabolite/ (time*volume*gDCW)). Significant advantages that might result from increasing productivity include, without limitation, a decrease in fermentor run time, a decrease in the size of fermentor required for production of equivalent amounts of secondary metabolite, or a decrease in the biomass required for production. Collectively, improvements in productivity can reduce both fixed costs (capital equipment expenses such as fermentor and production facility size, for example) and variable costs (including, but not limited to, decreased waste stream during downstream processing, decreased energy and labor costs, and decreased cost of bulk ingredients). Preferably, such increased productivity is by at least ten percent, more preferably at least 50 percent, and most preferably at least two-fold.

Preferably, for this aspect of the invention, when the secondary metabolite is isopenicillin N, then the modulation is not mediated by the transcription factor CPCR1; when the secondary metabolite is sterigmatocystin, then the modulation is not through AflR, FadA, or FluG; when the secondary metabolite is aflatoxin, then the modulation is not through AflR; when the secondary metabolite is penicillin and the fungus is *Aspergillus*, then the modulation is not through mutations that result in expression of truncated forms of PacC or constitutively active forms of FadA; when the gene involved in regulation of secondary metabolite production is from *Saccharomyces cerevisiae*, then the modulation is not through decreased activity or expression of Bem2, Hog1, Ira1, Rim15, Sfl1, Srb11, Ssd1, Swi4, Tpk3 or though increased activity or expression of Afl1, Cdc25, Dhh1, Hap4, Inv11, Inv13, Inv5, Inv7, Inv9, Mcm1, Mep2, Mga1, Msn1, Msn5, Mss11, Pet9, Pho23, Ptc1, Rim101, Rim13, Rim9, Snf8, Stp22, Tpk2, Vps28, Vps36, or Ypr1.

In certain embodiments of the methods according to this aspect of the invention, the modulation is overexpression of the gene. "Overexpression of the gene" is as used before. Preferred genes according to this aspect of the invention include, without limitation, AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "the gene acts on" is as used before. The term "transcription factor" is as used before. Preferred transcription factors include, without limitation, transcription factors that modulate the expression of genes involved in the production or response to the small molecule cAMP (preferred examples include, without limitation, Mga1, Msn2, Msn4, Sfl1, and Sok2); transcription factors that function downstream of mitogen-activated protein (MAP) kinase signaling pathways that regulate the yeast invasion response (preferred examples include, without limitation, Mcm1, Ste12, and Tec1); transcription factors that modulate the expression of genes involved in nitrogen regulation (preferred examples include, without limitation, AreA, Gln3, Hms1, Hms2, NreB, TamA, and Uga3); transcription factors that modulate the expression of genes involved in pH regulation in fungi (preferred examples include, without limitation PacC and Rim101); general transcription factors (preferred examples include, without limitation, Sin3, Snf2, Srb8, Srb9, Srb10, Srb11, Ssn6, and Tup1); transcription factors that modulate the expression of genes involved in carbon metabolism (preferred examples include, without limitation, Adr1, Cat8, CreA, FacB, Gcr1, Gcr2, Hap4, Mig1, Mig2, Mth1, Nrg1, Oaf1, and Sip4); heme-dependent transcription factors (preferred examples include, without limitation, Hap1 and Rox1); transcription factors that modulate the expression of genes involved in the uptake of metals (preferred examples include, without limitation, Aft1, Cup9, Mac1, SreP, SreA, and Zap1); transcription factors that modulate the expression of genes involved in cell-cycle regulation (preferred examples include, without limitation, Skn7, Swi4, and Swi6); transcription factors that modulate the expression of genes involved in invasion (preferred examples include, without limitation, Ash1, Flo8, Gts1, Inv7, Msn1, Mss11, Phd1, and Rre1); transcription factors that modulate the expression of genes involved in amino acid biosynthesis or transport (preferred examples include, without limitation, Gcn4, Leu3, Lys14, Met4, Met28, Met31, MetR, Put3, SconB, and Uga3); transcription factors that modulate the expression of genes involved in phosphate metabolism or transport (preferred examples include, without limitation, Pho2 and Pho4); transcription factors that modulate the expression of genes involved in nucleotide metabolism or transport (preferred examples include, without limitation, Ppr1 and UaY); transcription factors that modulate the expression of genes involved in cell wall processes (preferred examples include, without limitation, Ace2, Swi4, and Swi6); transcription factors that modulate the expression of genes involved in sporulation (preferred examples include, without limitation, Ime1 and Ime4); transcription factors that modulate the expression of genes involved in phospholipid synthesis (preferred examples include, without limitation, Ino2); transcription factors that modulate the expression of genes involved in aflatoxin biosynthesis (preferred examples include, without limitation, AflR); transcription factors that modulate the expression of genes involved in lovastatin biosynthesis (preferred examples include, without limitation, AAD34561 and LovE); and transcription factors that modulate the expression of genes involved in filamentous fungal development (preferred examples include, without limitation, AbaA). The term "general transcription factors" is as used before. The term "invasion" is as used before.

In certain embodiments of the methods according to this aspect of the invention, the gene either encodes a transmembrane transporter or the product that it encodes acts on a transmembrane transporter. The term "transmembrane transporter" is as used before. Preferred classes of transmembrane transporters include, without limitation, proteins of the ATP-binding cassette superfamily, members of the Major Facilitator Superfamily (MFS) that include, without limitation Pump1 and Pump2, P-type ATPases, members of the mitochondrial carrier family (MCF) that include, without limitation, Pet9 and AAD34562, ion channels, permeases that include, without limitation, Bap2, Hip1, Mep1, and Mep2; and components that transport sugars, ions, or metals.

In certain embodiments of the methods according to this aspect of the invention, the gene either encodes a kinase or the product that it encodes acts on a kinase. The term "kinase" is as used before. Preferred kinases include, without limitation, Cdc28, Elm1, Fus3, Gcn2, Hog1, Hsl1, Hxk2, Kss1, Pbs2, Pho85, Rim15, Ste7, Sch9, Snf1, Ste11, Ste20, Tpk1, Tpk2, and Tpk3.

In certain embodiments of the methods according to this aspect of the invention, the gene either encodes a G-protein or the product that it encodes acts on a G-protein. The term "G-protein" is as used before. Preferred G-proteins include, without limitation Cdc42, FadA, Gpa1, Gpa2, Ras1, and Ras2.

In certain embodiments of the methods according to this aspect of the invention, the gene either encodes a cell surface receptor or the product that it encodes acts on a cell surface receptor. The term "cell surface receptor" is as used before. Preferred cell surface receptors include, without limitation, G-protein coupled receptors. Preferred G-protein coupled receptors include, without limitation, Gpr1.

In certain embodiments of the methods according to this aspect of the invention, the gene either encodes a GTPase activating protein or the product that it encodes acts on a GTPase activating protein. The term "GTPase activating protein" is as used before. Preferred GTPase activating proteins include, without limitation, RGS family members. "RGS family members" are regulators of G-protein signaling that act upon G-protein coupled receptors. Preferred RGS family members include, without limitation, FlbA, Rgs2, and Sst2.

In certain embodiments of the methods according to this aspect of the invention, the gene either encodes a guanine nucleotide exchange factor or the product that it encodes acts on a guanine nucleotide exchange factor. The term "guanine nucleotide exchange factor" is as used before. Preferred guanine nucleotide exchange factors include, without limitation, Cdc24 and Cdc25.

In certain embodiments of the methods according to this aspect of the invention, the gene either encodes a phosphatase or the product that it encodes acts on a phosphatase. The term "phosphatase" is as used before. Preferred phosphatases include, without limitation, Cdc55 and Ptc1.

In certain embodiments of the methods according to this aspect of the invention, the gene either encodes a protease or the product that it encodes acts on a protease. The term "protease" is as used before. Preferred proteases include, without limitation, Rim13 and LF.

In certain embodiments of the methods according to this aspect of the invention, the gene either encodes a cyclic nucleotide phosphodiesterase or the product that it encodes acts on a cyclic nucleotide phosphodiesterase. The term "cyclic nucleotide phosphodiesterase" is as used before. Preferred examples of cyclic nucleotide phosphodiesterases include, without limitation, Pde2.

In certain embodiments of the methods according to this aspect of the invention, the gene either encodes a bacterial protein toxin or the product that it encodes acts on a bacterial protein toxin. The term "bacterial protein toxin" is as used before. Preferred bacterial protein toxins include, without limitation, Anthrax toxin edema factor (EF; *Bacillus anthracis*), Anthrax toxin lethal factor (LF; *Bacillus anthracis*), adenylate cyclase toxin (*Bordetella pertussis*), Cholera enterotoxin (*Vibrio cholerae*), LT toxin (*Escherichia coli*), ST toxin (*E. coli*), Shiga toxin (*Shigella dysenteriae*), Perfringens enterotoxin (*Clostridium perfringens*), Botulinum toxin (*Clostridium botulinum*), Tetanus toxin (*Clostridium tetani*), Diphtheria toxin (*Corynebacterium diphtheriae*), Exotoxin A (*Pseudomonas aeruginosa*), Exoenzyme S (*P. aeruginosa*), Pertussis toxin (*Bordetella pertussis*), alpha and epsilon toxins (*C. perfringens*), lethal toxin (LT; *Clostridium sordellii*), toxins A and B (*Clostridium dificile*), and phospholipase C (*Clostridium bifermentans*).

In certain embodiments of the methods according to this aspect of the invention, the gene either encodes an importin protein or the product that it encodes acts on an importin protein. The term "importin" protein is as used before. Preferred examples of importin proteins include, without limitation, Msn5.

In certain embodiments of the methods according to this aspect of the invention, the gene either encodes a RNA-binding protein or the product that it encodes acts on a RNA-binding protein. Preferred examples of RNA-binding proteins include, without limitation, Dhh1 and Whi3.

In certain embodiments of the methods according to this aspect of the invention, the gene either encodes a component of a SCF complex or the product that it encodes acts on a component of a SCF complex. The term "component of a SCF complex" is as used before. Preferred examples of components of a SCF complex include, without limitation, Grr1.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins and biosynthetic intermediates thereof. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, SFL1, SHO1, SHR3, SIN3, SIP4, SKN7, SNF1, SNF2, SNF7, SNF8, sconB, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes. The term "fungal homolog" is as used before.

In certain embodiments of the methods according to this aspect of the invention, the methods further comprise purifying the secondary metabolite from a culture of the fungus. The term "purifying" is as used before.

In a third aspect, the invention provides methods for improving production of a secondary metabolite in a fungus by increasing efflux or excretion of the secondary metabolite, the method comprising modulating the expression of a gene involved in regulation of secondary metabolite production in a manner that increases efflux or excretion of the secondary metabolite. "Increasing efflux or excretion of the secondary metabolite" means that a greater quantity of the secondary metabolite passes from the inside of the fungal cells to the outside of the fungal cell per unit time in the absence of lysis of the fungal cells. "Outside of the fungal cell" is defined as being no longer contained wholly within the lipid bilayer of the cell and/or extractable from the cell with methods that do not release a majority of intracellular contents. Increasing efflux of a metabolite could have beneficial impacts on the economics of a fermentation that include, but are not limited to, increasing the amount of metabolite available for isolation in the absence of cell lysis (thus reducing downstream processing costs) and elimination of negative autoregulation by the metabolite to allow increased synthesis.

In certain embodiments of the methods according to this aspect of the invention, the modulation is overexpression of the gene. "Overexpression of the gene" is as used before. Preferred genes according to this aspect of the invention include, without limitation, AAD34558, AAD34561, AAD34564, ATR1, ERG6, FCR1, GCN4, lovE, MDR1, PDR1, PDR3, PDR5, PDR10, PDR13, SNQ2, TRI12, and YAP1.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "transcription factor" is as used before. Preferred transcription factors include, without limitation, AAD34561, Fcr1, Gcn4, LovE, Pdr1, Pdr3, and Yap1.

In certain embodiments of the methods according to this aspect of the invention, the gene either encodes a transmembrane transporter or the product that it encodes acts on a transmembrane transporter. The term "transmembrane transporter" is as used before. Preferred transmembrane transporters include, without limitation, AAD34558, AAD34564, Atr1, Mdr1, Pdr5, Pdr10, Snq2, and Tri12.

In certain embodiments of the methods according to this aspect of the invention, the gene either encodes a kinase or the product that it encodes acts on a kinase. A "kinase" is as used before.

In certain embodiments of the methods according to this aspect of the invention, the gene either encodes a G-protein or the product that it encodes acts on a G-protein. A "G-protein" is as used before.

In certain embodiments of the methods according to this aspect of the invention, the gene either encodes a cell surface receptor or the product that it encodes acts on a cell surface receptor. A "cell surface receptor" is as used before.

In certain embodiments of the methods according to this aspect of the invention, the gene either encodes a GTPase activating protein or the product that it encodes acts on a GTPase activating protein. A "GTPase activating protein" is as used before.

In certain embodiments of the methods according to this aspect of the invention, the gene either encodes a guanine nucleotide exchange factor or the product that it encodes acts on a guanine nucleotide exchange factor. A "guanine nucleotide exchange factor" is as used before.

In certain embodiments of the methods according to this aspect of the invention, the gene either encodes a phosphatase or the product that it encodes acts on a phosphatase. A "phosphatase" is as used before.

In certain embodiments of the methods according to this aspect of the invention, the gene either encodes a protease or the product that it encodes acts on a protease. A "protease" is as used before.

In certain embodiments of the methods according to this aspect of the invention, the gene either encodes a cyclic nucleotide phosphodiesterase or the product that it encodes acts on a cyclic nucleotide phosphodiesterase. A "cyclic nucleotide phosphodiesterase" is as used before.

In certain embodiments of the methods according to this aspect of the invention, the gene either encodes a bacterial protein toxin or the product that it encodes acts on a bacterial protein toxin. A "bacterial protein toxin" is as used before.

In certain embodiments of the methods according to this aspect of the invention, the gene either encodes an importin protein or the product that it encodes acts on an importin protein. A "importin" protein is as used before.

In certain embodiments of the methods according to this aspect of the invention, the gene either encodes a RNA-binding protein or the product that it encodes acts on a RNA-binding protein.

In certain embodiments of the methods according to this aspect of the invention, the gene either encodes a component of a SCF complex or the product that it encodes acts on a component of a SCF complex. A "component of a SCF complex" is as used before.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of AAD34558, AAD34561, AAD34564, ATR1, ERG6, FCR1, GCN4, lovE, MDR1, PDR1, PDR3, PDR5, PDR10, PDR13, SNQ2, TRI12, YAP1, and any fungal homologs of the aforementioned genes. The term "fungal homolog" is as used before.

In certain embodiments of the methods according to this aspect of the invention, the methods further comprise purifying the secondary metabolite from a culture of the fungus. The term "purifying" is as used before.

In a fourth aspect, the invention provides methods for improving production of a secondary metabolite in a fungus by decreasing production of side products or non-desired secondary metabolites, the method comprising modulating the expression of a gene involved in regulation of secondary metabolite production in a manner that decreases production of side products or non-desired secondary metabolites.

In certain embodiments of the methods according to this aspect of the invention, the modulation is overexpression of the gene. "Overexpression of the gene" is as used before. Preferred genes according to this aspect of the invention include, without limitation, AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "the gene acts on" is as used before. The term "transcription factor" is as used before. Preferred transcription factors include, without limitation, transcription factors that modulate the expression of genes involved in the production or response to the small molecule cAMP (preferred examples include, without limitation, Mga1, Msn2, Msn4, Sfl1, and Sok2); transcription factors that function downstream of mitogen-activated protein (MAP) kinase signaling pathways that regulate the yeast invasion response (preferred examples include, without limitation, Mcm1, Ste12, and Tec1); transcription factors that modulate the expression of genes involved in nitrogen regulation (preferred examples include, without limitation, AreA, Gln3, Hms1, Hms2, NreB, TamA, and Uga3); transcription factors that modulate the expression of genes involved in pH regulation in fungi (preferred examples include, without limitation PacC and Rim101); general transcription factors (preferred examples include, without limitation, Sin3, Snf2, Srb8, Srb9, Srb10, Srb11, Ssn6, and Tup1); transcription factors that modulate the expression of genes involved in carbon metabolism (preferred examples include, without limitation, Adr1, Cat8, CreA, FacB, Gcr1, Gcr2, Hap4, Mig1, Mig2, Mth1, Nrg1, Oaf1, and Sip4); heme-dependent transcription factors (preferred examples include, without limitation, Hap1 and Rox1); transcription factors that modulate the expression of genes involved in the uptake of metals (preferred examples include, without limitation, Aft1, Cup9, Mac1, SreP, SreA, and Zap1); transcription factors that modulate the expression of genes involved in cell-cycle regulation (preferred examples include, without limitation, Skn7, Swi4, and Swi6); transcription factors that modulate the expression of genes involved in invasion (preferred examples include, without limitation, Ash1, Flo8, Gts1, Inv7, Msn1, Mss11, Phd1, and Rre1); transcription factors that modulate the expression of genes involved in amino acid biosynthesis or transport (preferred examples include, without limitation, Gcn4, Leu3, Lys14, Met4, Met28, Met31, MetR, Put3, SconB, and Uga3); transcription factors that modulate the expression of genes involved in phosphate metabolism or transport (preferred examples include, without limitation, Pho2 and Pho4); transcription factors that modulate the expression of genes involved in nucleotide metabolism or transport (preferred examples include, without limitation, Ppr1 and UaY); transcription factors that modulate the expression of genes involved in cell wall processes (preferred examples include, without limitation, Ace2, Swi4, and Swi6); transcription factors that modulate the expression of genes involved in sporulation (preferred examples include, without limitation, Ime1 and Ime4); transcription factors that modulate the expression of genes involved in phospholipid synthesis (preferred examples include, without limitation, Ino2); transcription factors that modulate the expression of genes involved in aflatoxin biosynthesis (preferred examples include, without limitation, AflR); transcription factors that modulate the expression of genes involved in lovastatin biosynthesis (preferred examples include, without limitation, AAD34561 and LovE); and transcription factors that modulate the expression of genes involved in filamentous fungal development (preferred examples include, without limitation, AbaA). The term "general transcription factors" is as used before. The term "invasion" is as used before.

In certain embodiments of the methods according to this aspect of the invention, the gene either encodes a transmembrane transporter or the product that it encodes acts on a transmembrane transporter. The term "transmembrane transporter" is as used before. Preferred classes of transmembrane transporters include, without limitation, proteins of the ATP-binding cassette superfamily, members of the Major Facilitator Superfamily (MFS) that include, without limitation Pump1 and Pump2, P-type ATPases, members of the mitochondrial carrier family (MCF) that include, without limitation, Pet9 and AAD34562, ion channels, permeases that include, without limitation, Bap2, Hip1, Mep1, and Mep2; and components that transport sugars, ions, or metals.

In certain embodiments of the methods according to this aspect of the invention, the gene either encodes a kinase or the product that it encodes acts on a kinase. The term "kinase" is as used before. Preferred kinases include, without limitation, Cdc28, Elm1, Fus3, Gcn2, Hog1, Hsl1, Hxk2, Kss1, Pbs2, Pho85, Rim15, Ste7, Sch9, Snf1, Ste11, Ste20, Tpk1, Tpk2, and Tpk3.

In certain embodiments of the methods according to this aspect of the invention, the gene either encodes a G-protein or the product that it encodes acts on a G-protein. The term "G-protein" is as used before. Preferred G-proteins include, without limitation Cdc42, FadA, Gpa1, Gpa2, Ras1, and Ras2.

In certain embodiments of the methods according to this aspect of the invention, the gene either encodes a cell surface receptor or the product that it encodes acts on a cell surface receptor. The term "cell surface receptor" is as used before. Preferred cell surface receptors include, without limitation, G-protein coupled receptors. Preferred G-protein coupled receptors include, without limitation, Gpr1.

In certain embodiments of the methods according to this aspect of the invention, the gene either encodes a GTPase activating protein or the product that it encodes acts on a GTPase activating protein. The term "GTPase activating protein" is as used before. Preferred GTPase activating proteins include, without limitation, RGS family members. "RGS family members" are regulators of G-protein signaling that act upon G-protein coupled receptors. Preferred RGS family members include, without limitation, FlbA, Rgs2, and Sst2.

In certain embodiments of the methods according to this aspect of the invention, the gene either encodes a guanine nucleotide exchange factor or the product that it encodes acts on a guanine nucleotide exchange factor. The term "guanine nucleotide exchange factor" is as used before. Preferred guanine nucleotide exchange factors include, without limitation, Cdc24 and Cdc25.

In certain embodiments of the methods according to this aspect of the invention, the gene either encodes a phosphatase or the product that it encodes acts on a phosphatase. The term "phosphatase" is as used before. Preferred phosphatases include, without limitation, Cdc55 and Ptc1.

In certain embodiments of the methods according to this aspect of the invention, the gene either encodes a protease or the product that it encodes acts on a protease. The term "protease" is as used before. Preferred proteases include, without limitation, Rim13 and LF.

In certain embodiments of the methods according to this aspect of the invention, the gene either encodes a cyclic nucleotide phosphodiesterase or the product that it encodes acts on a cyclic nucleotide phosphodiesterase. The term "cyclic nucleotide phosphodiesterase" is as used before. Preferred examples of cyclic nucleotide phosphodiesterases include, without limitation, Pde2.

In certain embodiments of the methods according to this aspect of the invention, the gene either encodes a bacterial protein toxin or the product that it encodes acts on a bacterial protein toxin. The term "bacterial protein toxin" is as used before. Preferred bacterial protein toxins include, without limitation, Anthrax toxin edema factor (EF; *Bacillus anthracis*), Anthrax toxin lethal factor (LF; *Bacillus anthracis*), adenylate cyclase toxin (*Bordetella pertussis*), Cholera enterotoxin (*Vibrio cholerae*), LT toxin (*Escherichia coli*), ST toxin (*E. coli*), Shiga toxin (*Shigella dysenteriae*), Perfringens enterotoxin (*Clostridium perfringens*), Botulinum toxin (*Clostridium botulinum*), Tetanus toxin (*Clostridium tetani*), Diphtheria toxin (*Corynebacterium diphtheriae*), Exotoxin A (*Pseudomonas aeruginosa*), Exoenzyme S (*P. aeruginosa*), Pertussis toxin (*Bordetella pertussis*), alpha and epsilon toxins (*C. perfringens*), lethal toxin (LT; *Clostridium sordellii*), toxins A and B (*Clostridium dificile*), and phospholipase C (*Clostridium bifermentans*).

In certain embodiments of the methods according to this aspect of the invention, the gene either encodes an importin protein or the product that it encodes acts on an importin protein. The term "importin" protein is as used before. Preferred examples of importin proteins include, without limitation, Msn5.

In certain embodiments of the methods according to this aspect of the invention, the gene either encodes a RNA-binding protein or the product that it encodes acts on a RNA-binding protein. Preferred examples of RNA-binding proteins include, without limitation, Dhh1 and Whi3.

In certain embodiments of the methods according to this aspect of the invention, the gene either encodes a component of a SCF complex or the product that it encodes acts on a component of a SCF complex. The term "component of a SCF complex" is as used before. Preferred examples of components of a SCF complex include, without limitation, Grr1.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of AAD34561, AAD34562, abaA, ACE2, ADR1, AFL1, aflR, AFT1, amyR, areA, ASH1, BAP2, BCY1, CAT8, CDC24, CDC25, CDC28, CDC42, CDC55, CLB2, creA, CTS1, CUP9, CYR1, DFG16, DHH1, DPH3, ELM1, facB, FLO1, FLO11, FLO8, FUS3, GCN2, GCN4, GCR1, GCR2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGS2, RIM101, RIM13, RIM15, RIM9, ROX1, RRE1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes. The term "fungal homolog" is as used before.

In certain embodiments of the methods according to this aspect of the invention, the methods further comprise purifying the secondary metabolite from a culture of the fungus. The term "purifying" is as used before.

In a fifth aspect, the invention provides methods for improving production of a secondary metabolite in a fungus by altering the characteristics of the fungus in a manner that is beneficial to the production of the secondary metabolite, the method comprising modulating the expression of a gene involved in regulation of secondary metabolite production in a manner that alters the characteristics of the fungus. "Altering the characteristics" means changing the morphology or growth traits of the fungus. Preferred alterations include, without limitation, those alterations that result in transition of the fungus from the hyphal to yeast form, those alterations that result in transition of the fungus from the yeast to hyphal form, alterations that lead to more or less hyphal branching, alterations that increase or decrease flocculence, adherence, cell buoyancy, surface area of the fungus, cell wall integrity and/or stability, pellet size, ability to grow at higher or lower temperatures, and alterations that increase the saturating growth density of a culture or rate of pellet formation.

In certain embodiments of the methods according to this aspect of the invention, the modulation is overexpression of the gene. "Overexpression of the gene" is as used before. Preferred genes according to this aspect of the invention include, without limitation, AAD34561, abaA, ACE2, ADR1, AFL1, aflR, AFT1, AGA1, AGA2, amyR, areA, ASH1, BAP2, BCY1, BEM1, BEM2, BEM3, BNI1, BUD2, BUD5, CAT8, CDC24, CDC25, CDC28, CDC42, CDC55, CLB2, creA, CTS1, CUP9, CYR1, DFG16, DHH1, DPH3, ELM1, facB, FLO1, FLO10, FLO11, FLO5, FLO8, FLO9, FUS3, GCN2, GCN4, GCR1, GCR2, GIC1, GIC2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS1, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGA1, RGS2, RHO1, RHO2, RHO3, RHO4, RIM101, RIM13, RIM15, RIM9, ROX1, RRE1, RSR1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE12, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "the gene acts on" is as used before. The term "transcription factor" is as used before. Preferred transcription factors include, without limitation, transcription factors that modulate the expression of genes involved in the production or response to the small molecule cAMP (preferred examples include, without limitation, Mga1, Msn2, Msn4, Sfl1, and Sok2); transcription factors that function downstream of mitogen-activated protein (MAP) kinase signaling pathways that regulate the yeast invasion response (preferred examples include, without limitation, Mcm1, Ste12, and Tec1); transcription factors that modulate the expression of genes involved in nitrogen regulation (preferred examples include, without limitation, AreA, Gln3, Hms1, Hms2, NreB, TamA, and Uga3); transcription factors that modulate the expression of genes involved in pH regulation in fungi (preferred examples include, without limitation PacC and Rim101); general transcription factors (preferred examples include, without limitation, Sin3, Snf2, Srb8, Srb9, Srb10, Srb11, Ssn6, and Tup1); transcription factors that modulate the expression of genes involved in carbon metabolism (preferred examples include, without limitation, Adr1, Cat8, CreA, FacB, Gcr1, Gcr2, Hap4, Mig1, Mig2, Mth1, Nrg1, Oaf1, and Sip4); heme-dependent transcription factors (preferred examples include, without limitation, Hap1 and Rox1); transcription factors that modulate the expression of genes involved in the uptake of metals (preferred examples include, without limitation, Aft1, Cup9, Mac1, SreP, SreA, and Zap1); transcription factors that modulate the expression of genes involved in cell-cycle regulation (preferred examples include, without limitation, Skn7, Swi4, and Swi6); transcription factors that modulate the expression of genes involved in invasion (preferred examples include, without limitation, Ash1, Flo8, Gts1, Inv7, Msn1, Mss11, Phd1, and Rre1); transcription factors that modulate the expression of genes involved in amino acid biosynthesis or transport (preferred examples include, without limitation, Gcn4, Leu3, Lys14, Met4, Met28, Met31, MetR, Put3, SconB, and Uga3); transcription factors that modulate the expression of genes involved in phosphate metabolism or transport (preferred examples include, without limitation, Pho2 and Pho4); transcription factors that modulate the expression of genes involved in nucleotide metabolism or transport (preferred examples include, without limitation, Ppr1 and UaY); transcription factors that modulate the expression of genes involved in cell wall processes (preferred examples include, without limitation, Ace2, Swi4, and Swi6); transcription factors that modulate the expression of genes involved in sporulation (preferred examples include, without limitation, Ime1 and Ime4); transcription factors that modulate the expression of genes involved in phospholipid synthesis (preferred examples include, without limitation, Ino2); transcription factors that modulate the expression of genes involved in aflatoxin biosynthesis (preferred examples include, without limitation, AflR); transcription factors that modulate the expression of genes involved in lovastatin biosynthesis (preferred examples include, without limitation, AAD34561 and LovE); and transcription factors that modulate the expression of genes involved in filamentous fungal development (preferred examples include, without limitation, AbaA). The term "general transcription factors" is as used before. The term "invasion" is as used before.

In certain embodiments of the methods according to this aspect of the invention, the gene either encodes a transmembrane transporter or the product that it encodes acts on a transmembrane transporter. The term "transmembrane transporter" is as used before. Preferred classes of transmembrane transporters include, without limitation, proteins of the ATP-binding cassette superfamily, members of the Major Facilitator Superfamily (MFS) that include, without limitation Pump1 and Pump2, P-type ATPases, members of the mitochondrial carrier family (MCF) that include, without limitation, Pet9, ion channels, permeases that include, without limitation, Bap2, Hip1, Mep1, and Mep2; and components that transport sugars, ions, or metals.

In certain embodiments of the methods according to this aspect of the invention, the gene either encodes a kinase or the product that it encodes acts on a kinase. The term "kinase" is as used before. Preferred kinases include, without limitation, Cdc28, Elm1, Fus3, Gcn2, Hog1, Hsl1, Hxk2, Kss1, Pbs2, Pho85, Rim15, Ste7, Sch9, Snf1, Ste11, Ste20, Tpk1, Tpk2, and Tpk3.

In certain embodiments of the methods according to this aspect of the invention, the gene either encodes a G-protein or the product that it encodes acts on a G-protein. The term "G-protein" is as used before. Preferred G-proteins include, without limitation Cdc42, FadA, Gpa1, Gpa2, Ras1, Ras2, Rho1, Rho2, Rho3, Rho4, and Rsr1.

In certain embodiments of the methods according to this aspect of the invention, the gene either encodes a cell surface receptor or the product that it encodes acts on a cell surface receptor. The term "cell surface receptor" is as used before. Preferred cell surface receptors include, without limitation, G-protein coupled receptors. Preferred G-protein coupled receptors include, without limitation, Gpr1.

In certain embodiments of the methods according to this aspect of the invention, the gene either encodes a GTPase activating protein or the product that it encodes acts on a GTPase activating protein. The term "GTPase activating protein" is as used before. Preferred GTPase activating proteins include, without limitation, RGS family members. The term "RGS family members" is as used before. Preferred RGS family members include, without limitation, FlbA, Rgs2, and Sst2. Preferred examples of non-RGS family GTPase-activating proteins include, without limitation, Bem2, Bem3, Bud2, Rga1, and Rga2.

In certain embodiments of the methods according to this aspect of the invention, the gene either encodes a guanine nucleotide exchange factor or the product that it encodes acts on a guanine nucleotide exchange factor. The term "guanine nucleotide exchange factor" is as used before. Preferred guanine nucleotide exchange factors include, without limitation, Bud5, Cdc24, and Cdc25.

In certain embodiments of the methods according to this aspect of the invention, the gene either encodes a phosphatase or the product that it encodes acts on a phosphatase. The term "phosphatase" is as used before. Preferred phosphatases include, without limitation, Cdc55 and Ptc1.

In certain embodiments of the methods according to this aspect of the invention, the gene either encodes a protease or the product that it encodes acts on a protease. The term "protease" is as used before. Preferred proteases include, without limitation, Rim13 and LF.

In certain embodiments of the methods according to this aspect of the invention, the gene either encodes a cyclic nucleotide phosphodiesterase or the product that it encodes acts on a cyclic nucleotide phosphodiesterase. The term "cyclic nucleotide phosphodiesterase" is as used before. Preferred examples of cyclic nucleotide phosphodiesterases include, without limitation, Pde2.

In certain embodiments of the methods according to this aspect of the invention, the gene either encodes a bacterial protein toxin or the product that it encodes acts on a bacterial protein toxin. The term "bacterial protein toxin" is as used before. Preferred bacterial protein toxins include, without limitation, Anthrax toxin edema factor (EF; *Bacillus anthracis*), Anthrax toxin lethal factor (LF; *Bacillus anthracis*), adenylate cyclase toxin (*Bordetella pertussis*), Cholera enterotoxin (*Vibrio cholerae*), LT toxin (*Escherichia coli*), ST toxin (*E. coli*), Shiga toxin (*Shigella dysenteriae*), Perfringens enterotoxin (*Clostridium perfringens*), Botulinum toxin (*Clostridium botulinum*), Tetanus toxin (*Clostridium tetani*), Diphtheria toxin (*Corynebacterium diphtheriae*), Exotoxin A (*Pseudomonas aeruginosa*), Exoenzyme S (*P. aeruginosa*), Pertussis toxin (*Bordetella pertussis*), alpha and epsilon toxins (*C. perfringens*), lethal toxin (LT; *Clostridium sordellii*), toxins A and B (*Clostridium dificile*), and phospholipase C (*Clostridium bifermentans*).

In certain embodiments of the methods according to this aspect of the invention, the gene either encodes an importin protein or the product that it encodes acts on an importin protein. The term "importin" protein is as used before. Preferred examples of importin proteins include, without limitation, Msn5.

In certain embodiments of the methods according to this aspect of the invention, the gene either encodes a RNA-binding protein or the product that it encodes acts on a RNA-binding protein. Preferred examples of RNA-binding proteins include, without limitation, Dhh1 and Whi3.

In certain embodiments of the methods according to this aspect of the invention, the gene either encodes a component of a SCF complex or the product that it encodes acts on a component of a SCF complex. The term "component of a SCF complex" is as used before. Preferred examples of components of a SCF complex include, without limitation, Grr1.

In certain embodiments of the methods according to this aspect of the invention, the gene either encodes an adherin or the product that it encodes acts on an adherin. The term "adherin" means a molecule that functions to promote the interaction of a cell with another component, including, without limitation, interaction with other cells of the same genotype, interaction with cells of a different genotype, and interaction with growth substrates. Preferred examples of adherins include, without limitation, Aga1, Aga2, Flo1, Flo10, Flo11, Flo5, and Flo9.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of AAD34561, abaA, ACE2, ADR1, AFL1, aflR, AFT1, AGA1, AGA2, amyR, areA, ASH1, BAP2, BCY1, BEM1, BEM2, BEM3, BNI1, BUD2, BUD5, CAT8, CDC24, CDC25, CDC28, CDC42, CDC55, CLB2, creA, CTS1, CUP9, CYR1, DFG16, DHH1, DPH3, ELM1, facB, FLO1, FLO10, FLO11, FLO5, FLO8, FLO9, FUS3, GCN2, GCN4, GCR1, GCR2, GIC1, GIC2, GLN3, GPA1, GPA2, GPR1, GRR1, GTS1, HAP1, HAP4, HIP1, HMS1, HMS2, HOG1, HSL1, HXK2, IME1, IME4, INO2, INV11, INV13, INV16, INV5, INV7, INV9, KSS1, LEU3, lovE, LYS14, MAC1, MCM1, MEP1, MEP2, MET28, MET31, MET4, metR, MGA1, MIG1, MIG2, MSN1, MSN2, MSN4, MSN5, MSS11, MTH1, NPR1, nreB, NRG1, OAF1, pacC, PBS2, PDE2, PET9, PHD1, PHO2, PHO4, PHO85, pkaR, PPR1, PTC1, PUT3, RAS1, RAS2, RGA1, RGS2, RHO1, RHO2, RHO3, RHO4, RIM101, RIM13, RIM15, RIM9, ROX1, RRE1, RSR1, SCH9, sconB, SFL1, SHO1, SHR3, SIN3, SIP4, SKN7, SNF1, SNF2, SNF7, SNF8, SOK2, SRB10, SRB11, SRB8, SRB9, sreA, sreP, SRV2, SSD1, SSN6, SST2, STE11, STE2, STE20, STE50, STE7, STP22, SWI4, SWI6, tamA, TEC1, TPK1, TPK2, TPK3, TUP1, UaY, UGA3, URE2, VPS28, VPS36, WHI3, YMR077c, YNL255c, YPR1, ZAP1, genes encoding bacterial protein toxins, and any fungal homologs of the aforementioned genes. The term "fungal homolog" is as used before.

In certain embodiments of the methods according to this aspect of the invention, the methods further comprise purifying the secondary metabolite from a culture of the fungus. The term "purifying" is as used before.

In a sixth aspect, the invention provides methods for improving production of a secondary metabolite in a fungus by causing conditional lysis of the fungus, the method comprising modulating the expression of a gene involved in regulation of secondary metabolite production in a manner that causes conditional lysis. "Causing conditional lysis" means causing the fungus to grow without lysis under a first set of growth conditions and to lyse under a second and different set of conditions, which are not lytic to the unmodified fungus. In preferred embodiments, the conditions that can be altered between the first and second growth conditions include, without limitation, the source or amount of nutrients such as carbon, nitrogen, and phosphate; the source or amount of specific enzymes; the source or amount of specific components found in cell walls; the amount of salts or osmolytes; the pH of the medium, the partial oxygen pressure, or temperature; and the amount of specific small molecules.

In certain embodiments of the methods according to this aspect of the invention, the modulation is overexpression of the gene. "Overexpression of the gene" is as used before. Preferred genes according to this aspect of the invention include, without limitation, ACE2, BCK1, BGL2, CHS1, CHS2, CHS3, CTS1, FKS1, GSC2, HOG1, ISR1, KRE6, MID2, MKK1, MKK2, PBS2, PKC1, PPH21, PPH22, PPZ1, PPZ2, PTP2, PTP3, RHO1, RLM1, ROM1, ROM2, SHO1, SKN1, SLG1, SLN1, SLT2, SMP1, SSK1, SSK2, SSK22, STE11, STT3, STT4, SWI4, SWI6, VPS45, WSC2, WSC3, WSC4, and YPD1.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "transcription factor" is as used before. Preferred transcription factors include, without limitation, Ace2, Rlm1, Smp1, Swi4, and Swi6.

In certain embodiments of the methods according to this aspect of the invention, the gene either encodes a transmembrane transporter or the product that it encodes acts on a transmembrane transporter. A "transmembrane transporter" is as used before.

In certain embodiments of the methods according to this aspect of the invention, the gene either encodes a kinase or the product that it encodes acts on a kinase. A "kinase" is as used before. Preferred kinases include, without limitation, Bck1, Hog1, Isr1, Mkk1, Mkk2, Pbs2, Pkc1, Slt2, Ssk2, and Ssk22.

In certain embodiments of the methods according to this aspect of the invention, the gene either encodes a component involved in cell wall biosynthesis or the product that it encodes acts on a component involved in cell wall biosynthesis. Preferred classes of components involved in cell wall biosynthesis include, without limitation, glucan synthases, glucanases, chitin synthase, and chitinases. Preferred examples of components involved in cell wall biosynthesis include, without limitation, Bgl2, Chs1, Chs2, Chs3, Cts1, Fks1, Gsc2, Kre6, and Skn1.

In certain embodiments of the methods according to this aspect of the invention, the gene either encodes a G-protein or the product that it encodes acts on a G-protein. A "G-protein" is a guanyl-nucleotide binding protein. Preferred G-proteins include, without limitation Rho1.

In certain embodiments of the methods according to this aspect of the invention, the gene either encodes a cell surface receptor or the product that it encodes acts on a cell surface receptor. A "cell surface receptor" is as used before. Preferred cell surface receptors include, without limitation, Sho1 and Sln1.

In certain embodiments of the methods according to this aspect of the invention, the gene either encodes a GTPase activating protein or the product that it encodes acts on a GTPase activating protein. A "GTPase activating protein" is as used before.

In certain embodiments of the methods according to this aspect of the invention, the gene either encodes a guanine nucleotide exchange factor or the product that it encodes acts on a guanine nucleotide exchange factor. A "guanine nucleotide exchange factor" is as used before. Preferred guanine nucleotide exchange factors include, without limitation, Rom1 and Rom2.

In certain embodiments of the methods according to this aspect of the invention, the gene either encodes a phosphatase or the product that it encodes acts on a phosphatase. A "phosphatase" is as used before. Preferred phosphatases include, without limitation, Pph21, Pph22, Ppz1, Ppz2, Ptp2, Ptp3, and Ptc1.

In certain embodiments of the methods according to this aspect of the invention, the gene either encodes a protease or the product that it encodes acts on a protease. A "protease" is as used before.

In certain embodiments of the methods according to this aspect of the invention, the gene either encodes a cyclic nucleotide phosphodiesterase or the product that it encodes acts on a cyclic nucleotide phosphodiesterase. A "cyclic nucleotide phosphodiesterase" is as used before.

In certain embodiments of the methods according to this aspect of the invention, the gene either encodes a bacterial protein toxin or the product that it encodes acts on a bacterial protein toxin. A "bacterial protein toxin" is as used before.

In certain embodiments of the methods according to this aspect of the invention, the gene either encodes an importin or the product that it encodes acts on an importin protein. A "importin" protein is as used before.

In certain embodiments of the methods according to this aspect of the invention, the gene either encodes a RNA-binding protein or the product that it encodes acts on a RNA-binding protein.

In certain embodiments of the methods according to this aspect of the invention, the gene either encodes a component of a SCF complex or the product that it encodes acts on a component of a SCF complex. A "component of a SCF complex" is as used before.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of ACE2, BCK1, BGL2, CHS1, CHS2, CHS3, CTS1, FKS1, GSC2, HOG1, ISR1, KRE6, MID2, MKK1, MKK2, PBS2, PKC1, PPH21, PPH22, PPZ1, PPZ2, PTP2, PTP3, RHO1, RLM1, ROM1, ROM2, SHO1, SKN1, SLG1, SLN1, SLT2, SMP1, SSK1, SSK2, SSK22, STE11, STT3, STT4, SWI4, SWI6, VPS45, WSC2, WSC3, WSC4, YPD1, and fungal homologs of the aforementioned genes. The term "fungal homolog" is as used before.

In certain embodiments of the methods according to this aspect of the invention, the methods further comprise purifying the secondary metabolite from a culture of the fungus. The term "purifying" is as used before.

In a seventh aspect, the invention provides methods for improving production of a secondary metabolite in a fungus by increasing the resistance of the fungus to the deleterious effects of exposure to a secondary metabolite made by the same organism, the method comprising modulating the expression of a gene involved in regulation of secondary metabolite production in a manner that increases resistance to the deleterious effects of exposure to a secondary metabolite. "Increasing the resistance of the fungus to the deleterious effects of exposure to a secondary metabolite" means to allow the fungus to survive, grow, or produce secondary metabolite in conditions that otherwise would be toxic or prevent production of secondary metabolite.

In certain embodiments of the methods according to this aspect of the invention, the modulation is overexpression of the gene. "Overexpression of the gene" is as used before. Preferred genes according to this aspect of the invention include, without limitation, AAD34558, AAD34561, AAD34564, ATR1, ERG6, ERG11, FCR1, GCN4, lovE, MDR1, PDR1, PDR3, PDR5, PDR10, PDR13, SNQ2, TRI12, YAP1, fungal homologs of the aforementioned genes, and genes that encode β-tubulin, calcineurin (including, without limitation, CNA1), chitin synthase, glucan synthase, HMG CoA reductase, N-terminal aminopeptidases, and RNA polymerase II.

In certain embodiments of the methods according to this aspect of the invention, the modulation is expression of a dominant mutation of the gene. The term "dominant mutation" is as used before. Preferred dominant mutations according to this aspect of the invention are as used before.

In certain embodiments of the methods according to this aspect of the invention, the modulation is mediated by a peptide modulator of gene expression. The term "peptide" is as used before. Peptides may be expressed in the cell or supplied exogenously. Preferably, they are provided on a scaffold to increase intracellular stability and to provide conformational constraint. Preferred peptides according to this aspect of the invention include those discussed earlier.

In certain embodiments of the methods according to this aspect of the invention, the peptide modulator is an activator of gene expression. The term "activator of gene expression" is as used before.

In certain embodiments of the methods according to this aspect of the invention, the peptide modulator is an inhibitor of gene expression. The term "inhibitor of gene expression" is as used before.

In certain embodiments of the methods according to this aspect of the invention, the modulation is mediated by a small molecule modulator of gene expression. In certain embodiments of the methods according to this aspect of the invention, the small molecule modulator is an activator of gene expression. The term "activator of gene expression" is as used before. In certain embodiments of the methods according to this aspect of the invention, the small molecule modulator is an inhibitor of gene expression. The term "inhibitor of gene expression" is as used before.

In certain embodiments of the methods according to this aspect of the invention, the modulation is conditional expression of the gene. The term "conditional expression" of a gene is as used before.

In certain embodiments of the methods according to this aspect of the invention, the gene either encodes a transcription factor or the product that it encodes acts on a transcription factor. The term "transcription factor" is as used before. Preferred transcription factors include, without limitation, AAD34561, Fcr1, Gcn4, LovE, Pdr1, Pdr3, and Yap1.

In certain embodiments of the methods according to this aspect of the invention, the gene either encodes a transmembrane transporter or the product that it encodes acts on a transmembrane transporter. The term "transmembrane transporter" is as used before. Preferred transmembrane transporters include, without limitation, AAD34558, AAD34564, Atr1, Mdr1, Pdr5, Pdr10, Snq2, and Tri12.

In certain embodiments of the methods according to this aspect of the invention, the gene either encodes a kinase or the product that it encodes acts on a kinase. A "kinase" is as used before.

In certain embodiments of the methods according to this aspect of the invention, the gene either encodes a G-protein or the product that it encodes acts on a G-protein. A "G-protein" is as used before.

In certain embodiments of the methods according to this aspect of the invention, the gene either encodes a cell surface receptor or the product that it encodes acts on a cell surface receptor. A "cell surface receptor" is as used before.

In certain embodiments of the methods according to this aspect of the invention, the gene either encodes a GTPase activating protein or the product that it encodes acts on a GTPase activating protein. A "GTPase activating protein" is as used before.

In certain embodiments of the methods according to this aspect of the invention, the gene either encodes a guanine nucleotide exchange factor or the product that it encodes acts on a guanine nucleotide exchange factor. A "guanine nucleotide exchange factor" is as used before.

In certain embodiments of the methods according to this aspect of the invention, the gene either encodes a phosphatase or the product that it encodes acts on a phosphatase. A "phosphatase" is as used before.

In certain embodiments of the methods according to this aspect of the invention, the gene either encodes a protease or the product that it encodes acts on a protease. A "protease" is as used before.

In certain embodiments of the methods according to this aspect of the invention, the gene either encodes a cyclic nucleotide phosphodiesterase or the product that it encodes acts on a cyclic nucleotide phosphodiesterase. A "cyclic nucleotide phosphodiesterase" is as used before.

In certain embodiments of the methods according to this aspect of the invention, the gene either encodes a bacterial protein toxin or the product that it encodes acts on a bacterial protein toxin. A "bacterial protein toxin" is as used before.

In certain embodiments of the methods according to this aspect of the invention, the gene either encodes an importin protein or the product that it encodes acts on an importin protein. An "importin" protein is as used before.

In certain embodiments of the methods according to this aspect of the invention, the gene either encodes a RNA-binding protein or the product that it encodes acts on a RNA-binding protein.

In certain embodiments of the methods according to this aspect of the invention, the gene either encodes a component of a SCF complex or the product that it encodes acts on a component of a SCF complex. A "component of a SCF complex" is as used before.

In certain embodiments of the methods according to this aspect of the invention, the gene either encodes or the gene product acts on a biosynthetic enzyme. In certain embodiments of the methods according to this aspect of the invention, the gene acts on biosynthetic enzyme for the secondary metabolite to be produced. The terms "biosynthetic enzyme" and "biosynthetic enzyme for the secondary metabolite to be produced" are as used before.

In certain embodiments of the methods according to this aspect of the invention, the secondary metabolite is an anti-bacterial. The term "anti-bacterial" is as used before. Preferred anti-bacterials include, without limitation, β-lactams. Prefererred β-lactams include, without limitation, penicillins and cephalosporins. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of the methods according to this aspect of the invention, the secondary metabolite is an anti-hypercholesterolemic or a biosynthetic intermediate thereof. An "anti-hypercholesterolemic" is as used before. Preferred anti-hypercholesterolemics include, without limitation, lovastatin, mevastatin, simvastatin, and pravastatin.

In certain embodiments of the methods according to this aspect of the invention, the secondary metabolite is an immunosuppressant or a biosynthetic intermediate thereof. An "immunosuppressant" is as used before. Preferred immunosuppressants include, without limitation, members of the cyclosporin family and beauverolide L. Preferred cyclosporins include, without limitation, cyclosporin A and cyclosporin C.

In certain embodiments of the methods according to this aspect of the invention, the secondary metabolite is an ergot alkaloid or a biosynthetic intermediate thereof. The term "ergot alkaloid" is as used before. Preferred classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocominine, ergonovine, ergometrinine, and ergoclavine.

In certain embodiments of the methods according to this aspect of the invention, the secondary metabolite is an inhibitor of angiogenesis or a biosynthetic intermediate thereof. The term "inhibitor of angiogenesis" is as used before. Preferred inhibitors of angiogenesis include, without limitation, fumagillin and ovalicin.

In certain embodiments of the methods according to this aspect of the invention, the secondary metabolite is a glucan synthase inhibitor or a biosynthetic intermediate thereof. The term "glucan synthase inhibitor" is as used before. Preferred glucan synthase inhibitors include, without limitation, echinocandin B, pneumocandin B, aculeacin A, and papulacandin.

In certain embodiments of the methods according to this aspect of the invention, the secondary metabolite is a member of the gliotoxin family of compounds or a biosynthetic intermediate thereof. The term "gliotoxin family of compounds" is as used before. Preferred members of the "gliotoxin family of compounds" include, without limitation, gliotoxin and aspirochlorine.

In certain embodiments of the methods according to this aspect of the invention, the secondary metabolite is a fungal toxin or a biosynthetic intermediate thereof. The term "fungal toxin" is as used before. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

In certain embodiments of the methods according to this aspect of the invention, the secondary metabolite is a modulator of cell surface receptor signaling or a biosynthetic intermediate thereof. The term "cell surface receptor" is as used before. Preferred modulators of cell surface signaling include, without limitation, the insulin receptor agonist L-783,281 and the cholecystokinin receptor antagonist asperlicin.

In certain embodiments of the methods according to this aspect of the invention, the secondary metabolite is a plant growth regulator or a biosynthetic intermediate thereof. The term "plant growth regulator" is as used before. Preferred plant growth regulators include, without limitation, cytokinin, auxin, gibberellin, abscisic acid, and ethylene.

In certain embodiments of the methods according to this aspect of the invention, the secondary metabolite is a pigment or a biosynthetic intermediate thereof. The term "pigment" is as defined before. Preferred pigments include, without limitation, melanins and carotenoids.

In certain embodiments of the methods according to this aspect of the invention, the secondary metabolite is an insecticide or a biosynthetic intermediate thereof. The term "insecticide" is as used before. Preferred insecticides include, without limitation, nodulisporic acid.

In certain embodiments of the methods according to this aspect of the invention, the secondary metabolite is an anti-neoplastic compound or a biosynthetic intermediate thereof. The term "anti-neoplastic" compound is as used before. Preferred anti-neoplastic compounds include, without limitation, taxol (paclitaxel) and related taxoids.

In certain embodiments of the methods according to this aspect of the invention, the gene is selected from the group consisting of AAD34558, AAD34561, AAD34564, ATR1, ERG6, ERG11, FCR1, GCN4, lovE, MDR1, PDR1, PDR3, PDR5, PDR10, PDR13, SNQ2, TRI12, YAP1, fungal homologs of the aforementioned genes, and genes that encode beta-tubulin, calcineurin (including, without limitation, CNA1), chitin synthase, glucan synthase, HMG CoA reductase, N-terminal aminopeptidases, and RNA polymerase II.

In certain embodiments of the methods according to this aspect of the invention, the methods further comprise purifying the secondary metabolite from a culture of the fungus. The term "purifying" is as used before.

In an eighth aspect, the invention provides genetically modified fungi, wherein the genetically modified fungi have an ability to produce secondary metabolites and the ability of the genetically modified fungus to produce secondary metabolites has been improved by any of the methods according to the invention.

In a ninth aspect, the invention provides a method for making a secondary metabolite, the method comprising culturing a fungus that is genetically modified according to the invention under conditions suitable for the production of secondary metabolites. "Conditions suitable for the production of secondary metabolites" means culture conditions under which the fungus does in fact produce one or more secondary metabolite.

The following examples are intended to further illustrate certain preferred embodiments of the invention and are not intended to limit the scope of the invention in any way.

EXAMPLE 1

Alteration of regulatory pathways modulating secondary metabolite production holds great promise to increase both the yield and productivity of secondary metabolites during fermentation. Importantly, enzymes required for biosynthesis of different metabolites during primary and secondary metabolism are often differentially regulated. For example, the plant *Ruta graveolens* has two different anthranilate synthase genes; one is expressed during primary metabolism to make tryptophan, whereas the second is specifically induced during secondary metabolism to promote the synthesis of acridone alkaloids (Bohlmann et al., Plant J. 7: 491–501 (1995)). Additionally, the lignin-degrading fungus *Phanerochaete chrysosporium* produces both manganese and lignin peroxidases during secondary metabolism. These peroxidases are induced differentially, both temporally and quantitatively, in response to carbon and nitrogen limitation (Pease et al., J. Bacteriol. 174: 3532–3540 (1992)). Expression of both manganese and lignin peroxidase families is induced by a rise in intracellular cAMP levels, although levels of cAMP required to induce lignin peroxidases are higher than those required to induce manganese peroxidases (Boominathan et al., Proc. Natl. Acad. Sci. USA 89: 5586–5590 (1992)). These and other examples of differential regulation of both primary and secondary metabolism and the biosynthesis of different secondary metabolites suggest that it is possible to inhibit the production of non-desirable primary and secondary metabolites while increasing the production of desirable secondary metabolites.

The fungus *Aspergillus terreus* produces a variety of secondary metabolites, including the polyketides lovastatin (Moore et al., J. Amer. Chem. Soc. 107: 3694–3701 (1985)), sulochrin (Curtis et al., J. Chem. Soc. [Perkin 1] 2:240–4 (1972)), and patulin (Borkowska Opacka and Escoula, Ann. Rech. Vet. 8: 129–33 (1977)). Lovastatin and its semisynthetic derivatives are widely prescribed and effective antihypercholesterolemic agents that are commercially produced by fermentation of *A. terreus*. It is thus desirable to develop strains of *A. terreus* that synthesize increased yields of lovastatin, with increased productivity and decreased levels of undesirable metabolites. Decreasing synthesis of alternative secondary metabolites can serve to both increase the primary metabolite pools available for lovastatin biosynthesis and to simplify purification of lovastatin from other metabolites in the fermentation broth.

It is possible to modulate the expression of a variety of regulators of secondary metabolism in order to increase lovastatin yield and productivity and decrease synthesis of non-desirable metabolites such as sulochrin in a fermentation of *A. terreus*. In one example, presented without limitation, overexpression of a cAMP-dependent protein kinase encoded by the *Saccharomyces cerevisiae* gene TPK2 is used. In wild-type *S. cerevisiae*, the intracellular levels of cAMP regulate Tpk2 activity. Under low concentrations of intracellular cAMP, Tpk2 is associated with Bcy1, a repressor of Tpk2 activity (Kuret et al., J. Biol. Chem. 263: 9149–54 (1988)). Association of cAMP with Bcy1 under conditions of elevated levels of intracellular levels of cAMP causes Bcy1 to dissociate from Tpk2, leading to activation of this kinase. Overexpression of TPK2 can override the cAMP requirement for activation of Tpk2 (Pan and Heitman, Mol. Cell. Biol. 19: 4874–87 (1999); Robertson and Fink, Proc. Natl. Acad. Sci. USA 95: 13783–7 (1998)).

To overexpress TPK2 in *Aspergillus terreus*, TPK2 is amplified using the polymerase chain reaction (PCR) with primers TPK2-1 5'-GAATTCATGGAATTCGTTGCAGAAAG-3' (SEQ ID NO: 1) and TPK2-2 5'-GGATCCTTAGAAATCTTGAAAGTATT-3' (SEQ ID NO: 2) using Turbo Pfu Polymerase (Stratagene) under standard reaction conditions described by the manufacturer. The resultant product is digested with restriction enzymes BamHI and EcoRI and cloned directly into BamHI/EcoRI-digested pLXZ161 DNA using methods well known to those skilled in the art, to generate plasmid pTPK2phleo. pLXZ161 is a gene vector derived from pBC-phleo (P. Silar, Fungal Genetics Newsletter 42: 73 (1995)) that carries a phleomycin resistance cassette for selection of transformants in *A. terreus*, as well as a polylinker located between the *Aspergillus nidulans* PGK promoter and the *A. nidulans* trpC terminator. pLXZ161 is constructed as follows: First, the *Aspergillus nidulans* trpC terminator is amplified from *A. nidulans* genomic DNA by the polymerase chain reaction (PCR) using Turbo Pfu Polymerase as described by the manufacturer (Stratagene). Primers used in this reaction are TRPC-1 5'-GCGGCCGCGGCGCCCGGCCCATGTCAACAAG AAT-3' (SEQ ID NO: 3) and TRPC-2 5'-CCGCGGCCGAGTGGAGATGTGGAGT-3' (SEQ ID NO: 4). The resultant product is digested with the restriction enzymes SacII and NotI, purified by agarose gel electrophoresis, and cloned into SacII/NotI-digested pBC-phleo DNA using methods well known to those skilled in the art, to generate pLXZ116. Second, the *A. nidulans* PGK promoter is amplified from *A. nidulans* genomic DNA by PCR using primers PGK1-1 5'-CATGGGGCCCCGTGATGTCTACCTGCCCAC-3' (SEQ ID NO: 5) and PGK1-2 5'-CATGATCGATTGTGGGTAGTTAATGGTATG-3' (SEQ ID NO: 6), Turbo Pfu Polymerase, and reaction conditions as described above. The resultant product is digested with ApaI and ClaI and cloned into ApaI/ClaI-digested pLXZ116 using methods well known to those skilled in the art, to generate pLXZ161.

For transformation of *A. terreus*, spores are first generated by culture of ATCC 20542 on petri plates containing potato dextrose agar (Difco) at 30° C. for 3–6 days. Spores are removed from PDA either by resuspension in sterile water or Tween-80 (0.1%) or by scraping directly from the plate using a sterile spatula. Yeast extract sucrose medium, or YES (2% Yeast Extract, 6% Sucrose), is inoculated to a density of 1–5×10$^6$ spores per ml and incubated with shaking in an Erlenmeyer flask at 26–30° C. for 12–16 hr (250 rpm). Mycelium is harvested by centrifugation at 3200 rpm for 10 minutes, and washed in sterile water two times. Mycelium is resuspended in a filter sterilized solution of Novozyme 234 (Sigma) at 2–5 mg/ml in 1 M MgSO$_4$ and digested at room temperature with shaking (80 rpm) for 1–2 hr. Undigested material is removed from the digest by filtration through Miracloth (Calbiochem). After adding 1–2 volumes of STC (0.8 M sorbitol, 25 mm Tris, pH 7.5, and 25 mM CaCl$_2$), the protoplasts are pelleted by centrifugation at 2500 rpm.

Protoplasts are washed 2 times in STC by centrifugation. Resulting protoplasts are resuspended to a density of $5 \times 10^7$ per ml in a solution of STC, SPTC (40% polyethylene glycol in STC) and DMSO in a ratio of 9:1:0.1 and frozen at −80° C.

Two aliquots (100 µl each) of protoplasts are mixed with 1–5 ug of either pTPK2phleo or pLXZ161 DNA and incubated on ice for 30 min. An aliquot of SPTC (15 µl) is added to each tube and the reaction is incubated at room temperature for 15 minutes. An additional aliquot (500 µl) is added with gentle mixing, and the reaction is incubated for an additional 15 minutes at room temperature: The reaction is next resuspended in 25 ml of molten regeneration medium (Potato Dextrose Agar from Sigma with 0.8 M sucrose, maintained at 50° C.), and poured onto a 150 mm petri plate containing 25 ml of solidified regeneration medium plus phleomycin (60–200 µg/ml). Transformants are typically visible after 2–5 days of incubation at 26–30° C.

To assess impact of overexpression of TPK2 on secondary metabolism, spore preps from twenty transformants from both the pTPK2phleo and pLXZ161 transformations are made. Each of these preps ($1 \times 10^7$ conidia/ml) is used to inoculate Erlenmeyer flasks (250 ml) containing 50 ml of production medium, composed of 10% glucose, 2% corn steep liquor, 5% tomato paste, and 2% beer yeast (Novak et al., 1997 Biotechnology Letters 19: 947–948). The flasks are incubated at 26° C. on a rotary shaker (250 rpm) for 7 days.

1 mL samples of fermentation broth are obtained every twenty-four hours over the twelve day growth of the transformant cultures in production media. After twelve days, the cell mass for each culture is separated from the broth by filtration, lyophilized and weighed. Lovastatin concentration in the whole broth (broth plus cell mass) from each of the time points is determined for every sample by measuring the amount of lovastatin in a fixed volume of fermentation broth by HPLC analysis, using lovastatin (open form) dissolved in 0.2M Tris buffer, pH 8/ethanol (2:1, v/v) to different concentrations to determine a standard curve. For each whole broth sample, the pH is adjusted to 7.7 and an equal volume of methanol is added. HPLC separation conditions are adapted from Friedrich et al. (J. Chromatogr. A. 704: 363–367 (1995)) and lovastatin is detected using a diode array spectrophotometer monitoring 237 nm. Lovastatin is separated from the other broth components on a spherisorb ODS-2 HPLC column using the following moble phase: potassium phosphate buffer (pH 7.7)-acetonitrile (65:35, v/v). Yield of lovastatin is expressed both as the amount of lovastatin per unit volume of broth after twelve days and also the amount of lovastatin per gram of dry cell weight of biomass at seven days. Productivity is determined by measuring the amount of lovastatin per unit volume of broth per gram of dry cell weight at each 24 hour time point of the fermentation and by expressing this concentration as a function of fermentation time. Transformants with increased productivity will show a higher concentration of lovastatin at earlier time points than seen for vector controls, although they need not show increased yield at seven days to exhibit increased productivity.

To determine the impact of TPK2 overexpression on sulochrin production the same whole broth/methanol extracts described above are assessed for concentration of sulochrin at the twelve day time points, also using HPLC analysis. Conditions for determining sulochrin concentrations by HPLC were developed by Vinci et al. (J. Ind. Microbiol. 8: 113–120 (1991)) and involve separation on a C-8 HPLC column using a mobile phase of 0.1% $H_3PO_4$-acetonitrile (40:60, v/v) and detecting at 235 nm.

EXAMPLE 2

Growth of a fungus that produces secondary metabolites can be limited, in part, by the toxic effects of the secondary metabolites themselves. In the absence of resistance mechanisms to protect fungi from toxic effects of these metabolites, decreased yields of the metabolite can be observed. For example, Alexander et al. (Mol. Gen. Genet. 261: 977–84 (1999)) have shown that the trichothecene efflux pump of *Fusarium sporotrichiodes*, encoded by the gene TRI12, is required both for high level production of, and resistance to the toxic effects of, trichothecenes produced by this fungus. Thus, modifications that increase the resistance of a fungus to a toxic secondary metabolite that it produces can increase the saturation density and extend the metabolically active lifetime of the producing fungus. In a bioreactor, such attributes will have the beneficial effect of increasing yield and productivity of a metabolite. Regulators of secondary metabolite production whose expression can be modulated to increase resistance of a fungus to toxic metabolites that it produces can include, without limitation, transporters that promote efflux of the metabolite from cells, enzymes that alter the chemical structure of the metabolite within cells to render it non-toxic, target(s) of the metabolite that mediate its toxicity, and gene products that alter cellular processes to counteract the toxic effects of a metabolite. Additional benefits of increasing efflux of secondary metabolites include increasing the amount of metabolite available for purification from the fermentation broth and mitigation of feedback inhibition of secondary metabolism that may be mediated by the metabolite itself. Indeed, feedback inhibition of a biosynthetic pathway by a product of that pathway is well documented in many microorganisms, and this inhibition can act at the transcriptional, translational, and post-translational levels. Several well-documented examples in yeast include the transcriptional repression of lysine biosynthetic genes by lysine (Feller et al., Eur. J. Biochem. 261: 163–70 (1999)), the decreased stability of both the mRNA encoding the uracil permease Fur4p and the permease itself in the presence of uracil (Seron et al., J. Bacteriol. 181: 1793–800 (1999)), and the inhibition of alpha-isopropyl malate synthase, a key step in leucine biosynthesis, by the presence of leucine (Beltzer et al., J. Biol. Chem. 263: 368–74 (1988)).

Transporters that could mediate resistance to secondary metabolites include members of the major facilitator superfamily (MFS) and the ATP binding cassette (ABC) transporters. For example, overexpression of the class I MFS-type transporter Flr1p in *S. cerevisiae* has been shown to confer resistance to a variety of toxic compounds such as cycloheximide, fluconazole, 4-nitroquinolone oxide, and cerulenin (Alarco et al., J. Biol. Chem. 272: 19304–13 (1997); Oskouian and Saba, Mol. Gen. Genet. 261: 346–53 (1999)). MFS transporters have been functionally grouped into 23 families in yeast, several of which contain members known or suspected to mediate resistance to toxic compounds by promoting their efflux from the cell (reviewed by Nelissen et al. in FEMS Microbiol. Rev. 21: 113–34 (1997)). Likewise, ABC transporters encoded by genes including PDR5 from *S. cerevisiae* (Boyum and Guidotti, Biochem. Biophys. Res. Commun. 230: 22–6 (1997)), PMR1 from *Penicillium digitatum* (Nakuane et al., Appl. Environ. Microbiol. 64: 3983–8 (1998)) and MDR1 from *Candida albicans* (Sanglard et al., Antimicrob. Agents Chemother. 39: 2378–86 (1995)), amongst others, have been shown to confer resistance to a variety of toxic compounds when their expression is increased. A complete cataloging of ABC transporters in yeast, as well as predicted function based on sequence similarities to transporters of known function, is described in (Decottignies and Goffeau, Nat. Genet. 15: 137–45 (1997)).

Transcription factors that regulate the expression of efflux pumps could also be used to increase efflux of a drug from a fungal cell to increase yields of a metabolite and decrease toxicity of the secondary metabolite in a fermentation. Such transcription factors include, but are not limited to, genes such as YAP1, PDR1, and PDR3 from S. cerevisiae and their homologs. Overexpression of each of these genes has been shown to upregulate expression of transporters and cause increased resistance of S. cerevisiae to toxic compounds (for examples, see Reid et al., J. Biol. Chem. 272: 12091–9 (1997); Katzmann et al., Mol. Cell. Biol. 14: 4653–61 (1994); Wendler et al., J. Biol. Chem. 272: 27091–8 (1997)).

Resistance to the toxic effects of secondary metabolites mediated through modulating expression of target genes will vary with metabolite. For example, amatoxins kill cells by inhibiting the function of the major cellular RNA polymerase, RNA polymerase II, in eucaryotic cells. Mutant forms of RNA polymerase II resistant to the effects of alpha-amanitin have been described (Bartolomei et al., Mol. Cell. Biol. 8: 330–9 (1988); Chen et al., Mol. Cell. Biol. 13: 4214–22 (1993)). Similarly, mutations affecting HMG CoA reductase, the target enzyme for the secondary metabolite lovastatin, have been identified. Increased levels of HMG CoA Reductase can also cause resistance to lovastatin (Ravid et al., J. Biol. Chem. 274: 29341–51 (1999); Lum et al., Yeast 12: 1107–24 (1996)). Taxol (paclitaxel), causes lethality by increasing microtubule stability, thus preventing exit from mitosis. Dominant mutations affecting β-tubulin that confer resistance to taxol have been characterized (for example, see Gonzalez et al., J. Biol. Chem. 274: 23875–82 (1999)) and could prove to be useful to confer resistance of production strains to this toxic metabolite. Such mutatations appear to decrease the stability of microtubules; whether these mutations affect the binding of taxol to microtubules is not known. Similarly, modulating expression of other genes that decrease the stability of microtubules could also confer taxol resistance to a fungus that produces taxol. The pneumocandin and echinocandin families of metabolites are fungal secondary metabolites that inhibit the enzyme 1,3-β-D-glucan synthase. Dominant mutations in the Candida albicans glucan synthase gene, FKS1, have been shown to confer resistance to candins (Douglas et al., Antimicrob. Agents Chemother. 41: 2471–9 (1997)). Glucan synthase mutations such as these could be used to generate fungal production strains with increased resistance to the candin class of antifungals. S. cerevisiae mutants resistant to the growth-inhibitory effects of the fungal secondary metabolite cyclosporin A have also been described (Cardenas et al., EMBO J 14: 2772–83 (1995)). These mutants were shown to harbor mutations in CNA1, the gene encoding the catalytic subunit of the heterodimeric calcium-calmodulin dependent phosphatase, calcineurin A. Fumagillin, an antiangiogenic agent, binds to and inhibits the N-terminal aminopeptidases in a wide variety of both procaryotes and eucaryotes (Sin et al., Proc. Natl. Acad. Sci. USA 94: 6099–103 (1997), Lowther et al., Proc. Natl. Acad. Sci. USA 95: 12153–7 (1998)). Mutations in this enzyme that block fumagillin binding and/or inhibitory activity could well prove useful in enhancing the resistance of fungal production strains to the growth inhibitory effects of this secondary metabolite.

To demonstrate the feasibility of engineering a fungal strain to be resistant to otherwise toxic amounts of a secondary metabolite, two genes from the lovastatin biosynthetic cluster of A. terreus strain ATCC 20542 were used (Kennedy et al., Science. 284: 1368–72 (1999)). These genes are predicted to encode proteins, denoted by Genbank accession numbers AAD34558 (hereafter referred to as PUMP1) and AAD34564 (hereby referred to as PUMP2), that are members of the MFS class of transporters. As described above, some MFS transporters are known to confer resistance to toxic compounds. PUMP1 and PUMP2 were tested for their ability to confer resistance to otherwise toxic levels of lovastatin when expressed in the fungus S. cerevisiae.

Aspergillus terreus (MF22; ATCC20542) was grown for 45 hours in Production Media at 25° C. (Production Media contains Cerelose, 4.5% (w/v) Peptonized Milk, 2.5% (w/v) Autolyzed yeast, 0.25% (w/v) Polyglycol P2000, 0.25% (w/v) pH to 7.0). Mycelia were harvested in a 50 cc syringe plugged with sterile cotton wool using a vacuum apparatus, washed once with sterile H2O, and snap frozen in liquid nitrogen. Mycelia were then ground to a powder under liquid nitrogen in a mortar and pestle, and homogenized in RLC buffer (Qiagen RNeasy Kit; Qiagen Inc., 28159 Avenue Stanford, Valencia Calif. 93155) using a GLH rotor-stator homogenizer (Omni International, 6530 Commerce Ct., Suite 100, Warrenton, Va. 20817.) Total RNA was purified using a RNeasy Maxi column according to the instructions of the manufacturer.

The polyA+ fraction of the A. terreus total RNA was isolated using Oligotex beads (Qiagen Inc.). Purified polyA+ RNA (5 μg) was used to generate complementary DNA (cDNA) using Superscript Reverse Transcriptase (Gibco BRL, 9800 Medical Center Drive, PO Box 6482, Rockville, Md. 20849) according to the instructions of the manufacturer. The cDNA was then used to isolate and clone PUMP1 and PUMP2 gene sequences using the polymerase chain reaction (PCR) and Gateway (Life Technologies) Cloning Technology (U.S. Pat. No. 5,888,732). Oligonucleotide sequences used for PCR were 5'-ACAAAAAAGCAGGCTCCACAATGACATCCCAC CACGGTGA-3' (SEQ ID NO: 7) and 5'-ACAAGAAAGCTGGGTTCATTCGCTCCGTCCTT TCT-3' (SEQ ID NO: 8) for PUMP1. Oligonucleotide sequences used for PUMP2 PCR were 5'-ACAAAAAAGCAGGCTCCACAATGGGCCGCGGT GACACTGA-3' (SEQ ID NO: 9) and 5'-ACAAGAAAGCTGGGTCTATTGGGTAGGCAGGT TGA-3' (SEQ ID NO: 10). The resultant plasmids, MB1333 and MB1334, were designed to express PUMP1 and PUMP2, respectively, under control of the S. cerevisiae TEF1 promoter. The plasmids carry a functional URA3 gene to allow for selection of the plasmid on media lacking uracil in a ura3 mutant strain. These plasmids also contained a 2-micron origin for high-copy replication in yeast. Control plasmids were as follows: MB969, the parent vector for MB1333 and MB1334, that does not contain a heterologous gene and is not expected to confer resistance to a yeast strain; MB1344, constructed and described in Donald et al., Appl. Environ. Microbiol. 63: 33414 (1997) as pRH127-3, that expresses a soluble form of HMG CoA reductase under control of the yeast GPD1 promoter and is known to confer resistance to increased levels of lovastatin (Donald et al., Appl. Environ. Microbiol. 63: 3341–4 (1997)).

MB1333, MB1334, MB969 and MB1344 were transformed into the yeast strain 22409 (Research Genetics, USA) using standard transformation methods for S. cerevisiae (Biotechniques, 1992, 13(1): 18). Strain 22409 is derived from the S288c strain background of S. cerevisiae, and its complete genotype is as follows: MATa/α, his3Δ1/ his3Δ1, leu2Δ1/leu2Δ0, ura3Δ0/ura3Δ0, LYS2/lys2Δ0, MET15/met15Δ0 pdr5::G418/PDR5. Transformants were grown overnight at 30° C. in synthetic complete media lacking uracil (SC-U) to maintain selection for the plasmid. Cultures were diluted 1:10 in sterile water, and 5 µl of each strain was spotted to SC-URA agar containing different concentrations of lovastatin as shown in FIG. 1. Strikingly, the strain harboring MB1333, and thus expressing PUMP1, shows resistance to lovastatin equivalent to the positive control strain in which the soluble fragment of HMG CoA reductase is overexpressed (strain carrying MB1344). These strains show no obvious growth inhibition even at the highest concentrations of lovastatin tested (150 µg/ml). In contrast, the vector-only control and the strain expressing PUMP2 show growth inhibition at the lowest concentration of lovastatin tested (50 µg/mL). Thus, these data indicate that PUMP1 is an excellent candidate for use in engineering lovastatin producing strains to enhance resistance to lovastatin and to promote efflux of this secondary metabolite.

EXAMPLE 3

Methods for improving the production of secondary metabolites can involve the construction of strains with desired characteristics for growth or recovery of secondary metabolites. Optimal strain characteristics likely will vary depending upon the fungus being utilized, the particular secondary metabolite being produced, and the specifications of an individual fermentation apparatus. Two traits that might be advantageous for maximal production of secondary metabolites are strains that can be lysed under specific conditions and strains that have morphological characteristics such as increased surface area of active growth and decreased hyphal length. Described below are examples of how both of these traits can be affected by modulating the activity of small GTP-binding proteins (G-proteins).

Fungi must respond to adverse external signals such as osmotic stress. Media for production of secondary metabolites often are hypo-osmotic, whereas fungi that exist on desiccated surfaces must respond to hyper-osmotic stress. One response to hyper-osmotic conditions is to increase the intracellular concentration of osmolytes such as glycerol. During hypo-osmotic stress the integrity of a fungal cell can be maintained both by decreasing intracellular osmolyte concentrations as well as by cell wall modifications. In Saccharomyces cerevisiae the PKC1-SLT2 signaling pathway is required for growth in conditions of low osmolarity (reviewed in Heinisch et al., Mol. Microbiol. 32: 671–680 (1999)). PKC1, which encodes yeast protein kinase C, is activated by components such as the small GTP-binding protein Rho1. Pkc1 then transduces this signal to a MAP kinase signaling cascade that includes the MEK kinase Bck1, the functionally redundant MEKs Mkk1 and Mkk2, and the MAP kinase Slt2. Mutations in genes encoding these signaling components result in varying degrees of cell lysis on media of low osmolarity. Genetic screens have identified many other proteins that function either upstream of PKC1-SLT2 signaling or regulate specific pathway components. These factors include Ppz1, Ppz2, Pph21, Pph22, Ptp2, Ptp3, Isr1, Rom1, Rom2, Mid2, Slg1, Wsc2, Wsc3, Wsc4, Stt3, Stt4, and Vps45; many of these components have homologs in other fungi. In addition, transcription factors, such as Rlm1, Swi4, and Swi6, that can function downstream of PKC1-SLT2 signaling have been identified, and it has been demonstrated that some of these factors are required for the proper expression of genes involved in cell wall biosynthesis. Thus, many components that can modulate the structural integrity of yeast cells have been identified. It is possible that manipulation of these factors could be performed, such that conditional expression of variants of these genes (or the homologs from filamentous fungi) would result in the lysis of fungi and maximal recovery of secondary metabolites.

Conditional lysis of fungi at the conclusion of a fermentor run would be a powerful method for promoting increased recovery of secondary metabolite. Preferably, conditional lysis would require a simple manipulation such as a change in a standard growth parameter (e.g. temperature, dissolved oxygen) or addition of an inexpensive solute. Examples of small molecules that may cause cell lysis include the protein kinase C inhibitor staurosporine, caffeine, dyes that bind the cell wall polymer chitin (e.g. calcofluor white, Congo red), inhibitors of glucan synthase (e.g. candins), and inhibitors of chitin synthase. The cost of using these molecules in a large-scale fermentor likely would be prohibitive. Similarly, addition of enzymes such as glucanases or chitinases would likely be an effective, but costly, method for inducing lysis. An alternative means to induce lysis would be the conditional expression of a dominant negative mutation in a gene encoding a component required for cell wall integrity. Since many components of the PKC1-SLT2 signaling pathway are widely conserved, it is possible that the conditional expression of a dominant inhibitory form of a member of this pathway would facilitate lysis in a variety of fungi, including those fungi that produce secondary metabolites such as lovastatin and cyclosporin A.

The G-protein Rho1 functions to regulate cell wall integrity by at least two independent mechanisms; Rho1 activates Pkc1 signaling as well as 1,3-beta-glucan synthase activity (Nonaka et al., EMBO J. 14: 5931–5938 (1995); Drgonova et al., Science 272: 277–279 (1996); Qadota et al., Science 272: 279–281 (1996)). In addition, dominant inhibitory forms of Rho1 have been identified. Expression of a rho1G22S D125N mutant form in a wild-type Saccharomyces cerevisiae strain results in cell lysis. Therefore, the conditional expression of dominant inhibitory forms of Rho1 under the control of a heat-shock inducible promoter might be an effective method for causing cell lysis in production fungi.

RHO1 coding sequence for construction of dominant mutations can be isolated from Saccharomyces cerevisiae genomic DNA. Primers 5'-cgcGGATCCCGACATATTCGAGGTTGACT-3' (SEQ ID NO: 11) and 5'-cccAAGCTTGCTAGAAATATGAACCTTCC-3' (SEQ ID NO: 12) are used to amplify RHO1 coding sequence with 1 kilobase of upstream regulatory sequence and 500 basepairs of downstream regulatory sequence. BamHI and HindIII restriction sites are added to the oligonucleotides to facilitate cloning into the pRS416 centromere-based yeast vector. The Quik Change Site-Directed Mutagenesis Kit (Stratagene, La Jolla Calif.) is used to first create a mutation that encodes the G22S substitution; next, the pRS416rho1G22S plasmid is used as a template to introduce a mutation that encodes the D125N substitution. Primer pair 5'-gtgcctgtAgtaagacatgt-3' (SEQ ID NO: 441)/5'-acatgtcttacTacaggcac-3' (SEQ ID NO: 442) is used to anneal to the pRS416RHO1 template for pRS416rho1G22S allele construction. Primer pair 5'-gtaaagtgAatttgagaaac-3' (SEQ ID NO: 443)/5'-gtttctcaaatTcactttac-3' (SEQ ID NO: 444) is used to anneal to the pRS416rho1G22S template for pRS416rho1G22S D125N allele construction. pRS416rho1G22S D125N and control plasmids (pRS416RHO1 and pRS416) are then used to transform a wild-type ura3 auxotrophic strain. Transformants are selected and grown at 25° C. in synthetic liquid growth medium lacking uracil and containing the osmolyte sorbitol (1M). Cultures are then transferred to growth in synthetic liquid growth medium lacking uracil without sorbitol, and cells are visually inspected following growth for various periods of time. Expression of the rho1G22S D125N dominant allele causes cell lysis after growth for approximately 120 minutes.

Conditional promoters can be used to express RHO1 dominant mutations in filamentous fungi. The *Aspergillus niger* tpsB gene is expressed at low levels during growth at ambient temperatures, whereas expression is strongly enhanced upon heat-shock at 40° C.; tpsB regulatory sequence contains multiple copies of the CCCCT stress responsive element (Wolschek et al., J. Biol. Chem. 272: 2729–2735 (1997)). Primers 5'-catgGGGCCCTCTCTCCACCGGCACTAAGATAGC-3' (SEQ ID NO: 13) and 5'-cgcGGATCCagCATTGGAAAAGGAGGGGGGGGA AG-3' (SEQ ID NO: 14) are used to amplify 490 basepairs of tpsB upstream regulatory sequence from *A. niger* genomic DNA. This PCR product contains the tpsB start codon followed by a BamHI cloning site. The tpsB upstream regulatory sequence can be cloned as an ApaI/BamHI fragment into the filamentous fungal vector pLXZ116 (see Example 1). The tpsB promoter is cloned into a multiple cloning site that also contains terminator sequence of the *A. nidulans* trpC gene. Primers 5'-cgcGGATCCaTCACAACAAGTTGGTAACAGTATC-3' (SEQ ID NO: 15) and 5'-ggACTAGTTAACAAGACACACTTCTTCTTCTT-3' (SEQ ID NO: 16) are used to amplify rho1G22S D125N coding sequence, and the product is cloned into the BamHI/SpeI sites of the tpsB containing filamentous fungal vector. This vector can be used to conditionally express (at 40° C.) a dominant negative form of Rho1 that can cause cell lysis.

The filamentous fungal vector containing the tpsB promoter (no RHO1 insert) and a vector containing rho1G22S D125N are used to transform *Aspergillus nidulans*, *Penicillium chrysogenum*, and *Aspergillus terreus*. To assess the impact of conditional expression of a RHO1 dominant negative mutation on cell wall integrity of filamentous fungi, mycelia or spore preps are made from 10 independent transformants, and mycelia or spores are used to inoculate both liquid shake flask cultures and plates containing minimal or rich medium. After growth for 1–2 days the strains are transferred to both 37° C. and 40° C. Strains are examined for morphological defects over the next 24 hours of incubation; potential morphological defects include abnormalities in polarized growth, hyphal wall integrity, and conidiophore development. The optimal time of heat-shock induction required for lysis will be determined. Furthermore, it will be determined whether any abnormalities can be suppressed by growth on medium containing osmotic stabilizers such as sorbitol (1.2 M), sucrose (1 M), or NaCl (1.5 M).

Transformants of *Aspergillus terreus* that display morphological abnormalities are used to assess whether conditional lysis of strains can be a tool for recovering larger quantities of lovastatin from fermentation broths. Five independent RHO1-containing transformants that display lysis defects will be processed as the *A. terreus* transformants described in earlier examples. Cultures from each transformant and control strains will be grown for either 8, 9, 10, 11, or 12 days, and cultures will then be incubated at the optimal temperature and for the optimal time required for cell lysis. Following heat shock the cell mass from each culture is separated from the broth by filtration, and the cell mass is lyophilized and weighed. Lovastatin concentration in the broth is calculated as described in earlier examples.

Morphological characteristics such as decreased hyphal length might be advantageous during production of secondary metabolites. For example, strains with shorter filament lengths should display decreased entanglement, floc formation, and shear stress. Such strains would be less susceptible to shear stress damage, these strains might reduce viscosity and facilitate mass transfer, and short filament strains might save energy costs required to power impellers. Increasing the amount of hyphal branching should result in an overall decrease in filament length. The following example describes how expression of a dominant inactive form of the *Saccharomyces cerevisiae* Rsr1 protein (also known as Bud1) results in increased lateral branch formation.

The yeast Rsr1 protein is required for proper bud site selection; strains lacking Rsr1 bud at random sites on the cell surface. Dominant negative mutations such as rsr1K16N have been identified, and expression of these mutant forms cause random bud site selection without causing obvious growth defects. Expression of rsr1K16N in filamentous fungi may increase branching, decrease filament length, and not have deleterious effects on the growth of the organism.

RSR1 coding sequence for construction of dominant mutations can be isolated from *Saccharomyces cerevisiae* genomic DNA. Primers 5'-cgcGGATCCTATCTTCACTCAATATACTTCCTA-3' (SEQ ID NO: 17) and 5'-cccAAGCTTCATCGTTGAAACTTGATAACGCAC-3' (SEQ ID NO: 18) are used to amplify RHO1 coding sequence with 750 basepairs of upstream regulatory sequence and 500 basepairs of downstream regulatory sequence. BamHI and HindIII restriction sites are added to the oligonucleotides to facilitate cloning into the pRS416 centromere-based yeast vector. The Quik Change Site-Directed Mutagenesis Kit (Stratagene, La Jolla Calif.) is used to create dominant-negative RSR1 substitution mutation K16N. Primer pair 5'-tggtgtcggtaaTtcctgcttaac-3' (SEQ ID NO: 445)/5'-gttaagcaggaAttaccgacacca-3' (SEQ ID NO: 446) is used to anneal to the pRS416RSR1 template for allele construction. The pRS416rsr1K16N and control pRS416 plasmids are then used to transform a haploid wild-type ura3 auxotrophic strain. Transformants are selected and grown at 30° C. in YPD liquid growth medium. Log phase cultures are fixed in 3.7% formaldehyde (vol:vol) and stained with the chitin-binding dye Calcofluor white, as described; previous sites of bud formation are marked with a chitin-rich structure called a bud scar. Fluorescent microscopy reveals that cells containing the control plasmid display clustering of bud scars at one pole of the cells, the well-characterized haploid pattern of bud site selection. Cells expressing rsr1K16N display a random pattern of bud site selection; bud scars are scattered across the surface of haploid cells. Cells expressing rsr1K16N do not display other obvious growth or morphological defects.

The *Aspergillus nidulans* PGK promoter can be used to express RSR1 dominant mutations in filamentous fungi. A filamentous fungal vector containing a multiple cloning site that is flanked by the PGK promoter and terminator sequence of the *A. nidulans* trpC gene is used. Primers 5'-cgcGGATCCGACTAATGAGAGACTATAAATTAG-3' (SEQ ID NO: 19) and 5'-ccgCTCGAGCTATAGAATAGTGCAAGTGGAAGC-3' (SEQ ID NO: 20) are used to amplify rsr1K16N coding sequence, and the product is cloned into the BamHI/XhoI sites of the filamentous fungal vector. This vector can be used to express a dominant negative form of Rsr1 that will affect the process of selecting sites for polarized growth.

The filamentous fungal vector containing rsr1K16N and control vector are used to transform *Aspergillus nidulans, Penicillium chrysogenum*, and *Aspergillus terreus*. To assess the impact of expression of RSR1 dominant negative mutations on lateral branch formation and filament length, mycelia and spore preps are made from 10 independent PCR-positive transformants, and mycelia and spores are used to inoculate both liquid shake flask cultures and plates containing minimal or rich medium. Strains are examined at various timepoints over a 48 hour period for morphological alterations, including altered patterns of germ tube emergence, increased lateral branching, decreased filament length, alterations in hyphal width, and changes in chitin staining pattern. Strains displaying desirable morphological changes are then tested in shake flask conditions to determine whether levels of penicillin (*A. nidulans, P. chrysogenum*) or lovastatin (*A. terreus*) production have changed significantly.

*Aspergillus terreus* and *Penicillium chrysogenum* transformants that display morphological characteristics such as decreased filament length and produce expected or greater levels of lovastatin and penicillin, respectively, are used to assess whether morphological changes can impact upon bioreactor challenges such as shear stress damage, mass transfer, and energy costs. Five independent PCR-positive RSR1-containing transformants that display morphological alterations are grown in a small-scale bioreactor, and examined for improved fermentation characteristics and/or production of secondary metabolite.

TABLE 1

| Gene | Sequence ID | Organism |
| --- | --- | --- |
| PUMP1 | AAD34558 | *Aspergillus terreus* |
| PUMP2 | AAD34564 | *Aspergillus terreus* |
| AAD34561 | AAD34561 | *Aspergillus terreus* |
| AAD34562 | AAD34562 | *Aspergillus terreus* |
| abaA | g1351833 | *Aspergillus nidulans* |
| ACE2 | YLR131c | *Saccharomyces cerevisiae* |
| ADR1 | YDR216w | *Saccharomyces cerevisiae* |
| AFL1 | YEL007w | *Saccharomyces cerevisiae* |
| aflR | g1703202 | *Aspergillus nidulans* |
| AFT1 | YGL071w | *Saccharomyces cerevisiae* |
| amyR | g4996624 | *Aspergillus nidulans* |
| areA | g1351972 | *Aspergillus nidulans* |
| ASH1 | YKL185w | *Saccharomyces cerevisiae* |
| ATR1 | YML116w | *Saccharomyces cerevisiae* |
| BAP2 | YBR068c | *Saccharomyces cerevisiae* |
| BCK1 | YJL095w | *Saccharomyces cerevisiae* |
| BCY1 | YIL033c | *Saccharomyces cerevisiae* |
| BEM2 | YER155c | *Saccharomyces cerevisiae* |
| BGL2 | YGR282c | *Saccharomyces cerevisiae* |
| CAT8 | YMR280c | *Saccharomyces cerevisiae* |
| CDC24 | YAL041w | *Saccharomyces cerevisiae* |
| CDC25 | YLR310c | *Saccharomyces cerevisiae* |
| CDC28 | YBR160w | *Saccharomyces cerevisiae* |
| CDC42 | YLR229c | *Saccharomyces cerevisiae* |
| CDC55 | YGL190c | *Saccharomyces cerevisiae* |
| CHS1 | YNL192w | *Saccharomyces cerevisiae* |
| CHS2 | YBR038w | *Saccharomyces cerevisiae* |
| CHS3 | YBR023c | *Saccharomyces cerevisiae* |
| CLB2 | YPR119w | *Saccharomyces cerevisiae* |
| creA | g168035 | *Aspergillus nidulans* |
| CTS1 | YLR286c | *Saccharomyces cerevisiae* |
| CUP9 | YPL177c | *Saccharomyces cerevisiae* |
| CYR1 | YJL005w | *Saccharomyces cerevisiae* |
| DFG16 | YOR030w | *Saccharomyces cerevisiae* |
| DHH1 | YDL160c | *Saccharomyces cerevisiae* |
| DPH3 | see PCT publication No. WO99/*** | *Saccharomyces cerevisiae* |

TABLE 1-continued

| Gene | Sequence ID | Organism |
| --- | --- | --- |
| ELM1 | YKL048c | *Saccharomyces cerevisiae* |
| ERG6 | YML008c | *Saccharomyces cerevisiae* |
| facB | g2262191 | *Aspergillus nidulans* |
| FCR1 | g4071315 | *Candida albicans* |
| FKS1 | YLR342w | *Saccharomyces cerevisiae* |
| FLO1 | YAR050w | *Saccharomyces cerevisiae* |
| FLO10 | YKR102w | *Saccharomyces cerevisiae* |
| FLO11 | YIR019c | *Saccharomyces cerevisiae* |
| FLO5 | YHR211w | *Saccharomyces cerevisiae* |
| FLO8 | YER108c | *Saccharomyces cerevisiae* |
| FLO9 | YAL063c | *Saccharomyces cerevisiae* |
| FUS3 | YBL016w | *Saccharomyces cerevisiae* |
| GCN2 | YDR283c | *Saccharomyces cerevisiae* |
| GCN4 | YEL009c | *Saccharomyces cerevisiae* |
| GCR1 | YPL075w | *Saccharomyces cerevisiae* |
| GCR2 | YNL199c | *Saccharomyces cerevisiae* |
| GLN3 | YER040w | *Saccharomyces cerevisiae* |
| GPA1 | YHR005c | *Saccharomyces cerevisiae* |
| GPA2 | YER020w | *Saccharomyces cerevisiae* |
| GPR1 | YDL035c | *Saccharomyces cerevisiae* |
| GRR1 | YJR090c | *Saccharomyces cerevisiae* |
| GSC2 | YGR032w | *Saccharomyces cerevisiae* |
| GTS1 | YGL181w | *Saccharomyces cerevisiae* |
| HAP1 | YLR256w | *Saccharomyces cerevisiae* |
| HAP4 | YKL109w | *Saccharomyces cerevisiae* |
| HIP1 | YGR191w | *Saccharomyces cerevisiae* |
| HMS1 | YOR032c | *Saccharomyces cerevisiae* |
| HMS2 | YJR147w | *Saccharomyces cerevisiae* |
| HOG1 | YLR113w | *Saccharomyces cerevisiae* |
| HSL1 | YKL101w | *Saccharomyces cerevisiae* |
| HXK2 | YGL253w | *Saccharomyces cerevisiae* |
| IME1 | YJR094c | *Saccharomyces cerevisiae* |
| IME4 | YGL192w | *Saccharomyces cerevisiae* |
| INO2 | YDR123c | *Saccharomyces cerevisiae* |
| INV11 | YNL294c | *Saccharomyces cerevisiae* |
| INV13 | YJR102c | *Saccharomyces cerevisiae* |
| INV16 | not cloned | *Saccharomyces cerevisiae* |
| INV5 | YOR275c | *Saccharomyces cerevisiae* |
| INV7 | YDL233w | *Saccharomyces cerevisiae* |
| INV9 | YGL046w + YGL045w | *Saccharomyces cerevisiae* |
| IRA1 | YBR140c | *Saccharomyces cerevisiae* |
| ISR1 | YPR106w | *Saccharomyces cerevisiae* |
| KRE6 | YPR159w | *Saccharomyces cerevisiae* |
| KSS1 | YGR040w | *Saccharomyces cerevisiae* |
| LEU3 | YLR451w | *Saccharomyces cerevisiae* |
| lovE | AAD34557 | *Aspergillus terreus* |
| LYS14 | YDR034c | *Saccharomyces cerevisiae* |
| MAC1 | YMR021c | *Saccharomyces cerevisiae* |
| MCM1 | YMR043w | *Saccharomyces cerevisiae* |
| MDR1 | g3378546 | *Candida albicans* |
| MEP1 | YGR121c | *Saccharomyces cerevisiae* |
| MEP2 | YNL142w | *Saccharomyces cerevisiae* |
| MET28 | YIR017c | *Saccharomyces cerevisiae* |
| MET31 | YPL038w | *Saccharomyces cerevisiae* |
| MET4 | YNL103w | *Saccharomyces cerevisiae* |
| metR | g5051964 | *Aspergillus nidulans* |
| MGA1 | YGR249w | *Saccharomyces cerevisiae* |
| MID2 | YLR332w | *Saccharomyces cerevisiae* |
| MIG1 | YGL035c | *Saccharomyces cerevisiae* |
| MIG2 | YGL209w | *Saccharomyces cerevisiae* |
| MKK1 | YOR231w | *Saccharomyces cerevisiae* |
| MKK2 | YPL140c | *Saccharomyces cerevisiae* |
| MSN1 | YOL116w | *Saccharomyces cerevisiae* |
| MSN2 | YMR037c | *Saccharomyces cerevisiae* |
| MSN4 | YKL062w | *Saccharomyces cerevisiae* |
| MSN5 | YDR335w | *Saccharomyces cerevisiae* |
| MSS11 | YMR164c | *Saccharomyces cerevisiae* |
| MTH1 | YDR277c | *Saccharomyces cerevisiae* |
| NPR1 | YNL183c | *Saccharomyces cerevisiae* |
| nreB | g3004634 | *Penicillium chrysogenum* |
| NRG1 | YDR043c | *Saccharomyces cerevisiae* |
| OAF1 | YAL051w | *Saccharomyces cerevisiae* |
| pacC | g3641619 | *Penicillium chrysogenum* |
| PBS2 | YJL128c | *Saccharomyces cerevisiae* |
| PDE2 | YOR360c | *Saccharomyces cerevisiae* |
| PDR1 | YGL013c | *Saccharomyces cerevisiae* |

TABLE 1-continued

| Gene | Sequence ID | Organism |
|---|---|---|
| PDR10 | YOR328w | Saccharomyces cerevisiae |
| PDR13 | YHR064c | Saccharomyces cerevisiae |
| PDR3 | YBL005w | Saccharomyces cerevisiae |
| PDR5 | YOR153w | Saccharomyces cerevisiae |
| PET9 | YBL030c | Saccharomyces cerevisiae |
| PHD1 | YKL043w | Saccharomyces cerevisiae |
| PHO2 | YDL106c | Saccharomyces cerevisiae |
| PHO23 | YNL097c | Saccharomyces cerevisiae |
| PHO4 | YFR034c | Saccharomyces cerevisiae |
| PHO85 | YPL031c | Saccharomyces cerevisiae |
| pkaR | g3170248 | Aspergillus nidulans |
| PKC1 | YBL105c | Saccharomyces cerevisiae |
| PPH21 | YDL134c | Saccharomyces cerevisiae |
| PPH22 | YDL188c | Saccharomyces cerevisiae |
| PPR1 | YLR014c | Saccharomyces cerevisiae |
| PPZ1 | YML016c | Saccharomyces cerevisiae |
| PPZ2 | YDR436w | Saccharomyces cerevisiae |
| PTC1 | YDL006w | Saccharomyces cerevisiae |
| PTP2 | YOR208w | Saccharomyces cerevisiae |
| PTP3 | YER075c | Saccharomyces cerevisiae |
| PUT3 | YKL015w | Saccharomyces cerevisiae |
| RAS1 | YOR101w | Saccharomyces cerevisiae |
| RAS2 | YNL098c | Saccharomyces cerevisiae |
| RGS2 | YOR107w | Saccharomyces cerevisiae |
| RHO1 | YPR165w | Saccharomyces cerevisiae |
| RIM101 | YHL027w | Saccharomyces cerevisiae |
| RIM13 | YMR154c | Saccharomyces cerevisiae |
| RIM15 | YFL033c | Saccharomyces cerevisiae |
| RIM9 | YMR063w | Saccharomyces cerevisiae |
| RLM1 | YPL089c | Saccharomyces cerevisiae |
| ROM1 | YGR070w | Saccharomyces cerevisiae |
| ROM2 | YLR371w | Saccharomyces cerevisiae |
| ROX1 | YPR065w | Saccharomyces cerevisiae |
| RRE1 | YGL096w | Saccharomyces cerevisiae |
| SCH9 | YHR205w | Saccharomyces cerevisiae |
| sconB | g1041197 | Aspergillus nidulans |
| SFL1 | YOR140w | Saccharomyces cerevisiae |
| SHO1 | YER118c | Saccharomyces cerevisiae |
| SHR3 | YDL212w | Saccharomyces cerevisiae |
| SIN3 | YOL004w | Saccharomyces cerevisiae |
| SIP4 | YJL089w | Saccharomyces cerevisiae |
| SKN1 | YGR143w | Saccharomyces cerevisiae |
| SKN7 | YHR206w | Saccharomyces cerevisiae |
| SLG1 | YOR008c | Saccharomyces cerevisiae |
| SLN1 | YIL147c | Saccharomyces cerevisiae |
| SLT2 | YHR030c | Saccharomyces cerevisiae |
| SMP1 | YBR182c | Saccharomyces cerevisiae |
| SNF1 | YDR477w | Saccharomyces cerevisiae |
| SNF2 | YOR290c | Saccharomyces cerevisiae |
| SNF7 | YLR025w | Saccharomyces cerevisiae |
| SNF8 | YPL002c | Saccharomyces cerevisiae |
| SNQ2 | YDR011w | Saccharomyces cerevisiae |
| SOK2 | YMR016c | Saccharomyces cerevisiae |
| SRB10 | YPL042c | Saccharomyces cerevisiae |
| SRB11 | YNL025c | Saccharomyces cerevisiae |
| SRB8 | YCR081w | Saccharomyces cerevisiae |
| SRB9 | YDR443c | Saccharomyces cerevisiae |
| sreA | g4585213 | Aspergillus nidulans |
| sreP | g1517916 | Penicillium chrysogenum |
| SRV2 | YNL138w | Saccharomyces cerevisiae |
| SSD1 | YDR293c | Saccharomyces cerevisiae |
| SSK1 | YLR006c | Saccharomyces cerevisiae |
| SSK2 | YNR031c | Saccharomyces cerevisiae |
| SSK22 | YCR073c | Saccharomyces cerevisiae |
| SSN6 | YBR112c | Saccharomyces cerevisiae |
| SST2 | YLR452c | Saccharomyces cerevisiae |
| STE11 | YLR362w | Saccharomyces cerevisiae |
| STE12 | YHR084w | Saccharomyces cerevisiae |
| STE20 | YHL007c | Saccharomyces cerevisiae |
| STE50 | YCL032w | Saccharomyces cerevisiae |
| STE7 | YDL159w | Saccharomyces cerevisiae |
| STP22 | YCL008c | Saccharomyces cerevisiae |
| STT3 | YGL022w | Saccharomyces cerevisiae |
| STT4 | YLR305c | Saccharomyces cerevisiae |
| SWI4 | YER111c | Saccharomyces cerevisiae |
| SWI6 | YLR182w | Saccharomyces cerevisiae |
| tamA | g4027860 | Aspergillus nidulans |
| TEC1 | YBR083w | Saccharomyces cerevisiae |
| TPK1 | YJL164c | Saccharomyces cerevisiae |
| TPK2 | YPL203w | Saccharomyces cerevisiae |
| TPK3 | YKL166c | Saccharomyces cerevisiae |
| TRI12 | g4225855 | Fusarium sporotrichioides |
| TUP1 | YCR084c | Saccharomyces cerevisiae |
| UaY | g695414 | Aspergillus nidulans |
| UGA3 | YDL170w | Saccharomyces cerevisiae |
| URE2 | YNL229c | Saccharomyces cerevisiae |
| VPS28 | YPL065w | Saccharomyces cerevisiae |
| VPS36 | YLR417w | Saccharomyces cerevisiae |
| VPS45 | YGL095c | Saccharomyces cerevisiae |
| WHI3 | YNL197c | Saccharomyces cerevisiae |
| WSC2 | YNL283c | Saccharomyces cerevisiae |
| WSC3 | YOL105c | Saccharomyces cerevisiae |
| WSC4 | YHL028w | Saccharomyces cerevisiae |
| YAP1 | YML007w | Saccharomyces cerevisiae |
| YMR077c | YMR077c | Saccharomyces cerevisiae |
| YNL255c | YNL255c | Saccharomyces cerevisiae |
| YPD1 | YDL235c | Saccharomyces cerevisiae |
| YPR1 | YDR368w | Saccharomyces cerevisiae |
| ZAP1 | YJL056c | Saccharomyces cerevisiae |

What is claimed is:

1. A method comprising:
   (a) modulating the production of a polyketide produced by a fungal cell by genetically modifying the fungal cell to conditionally express CreA or a fungal homolog thereof;
   (b) culturing the genetically modified fungal cell in culture medium under conditions suitable for the production of the polyketide; and
   (c) isolating a fraction of culture medium containing the polyketide.

2. The method of claim 1 wherein the polyketide is a statin.

3. The method of claim 2 wherein the statin is a lovastatin.

4. The method of any one of claims 1, 2 and 3 wherein the fungal cells is genetically modified to conditionally express CreA.

5. The method of claim 4 wherein the fungal cell is an *Ascomycete*.

6. The method of claim 5 wherein the *Ascomycete* is *A. terreus*.

7. A method comprising:
   (a) modulating the production of a polyketide produced by a fungal cell by genetically modifying the fungal cell to overexpress CreA or a fungal homolog thereof;
   (b) culturing the genetically modified fungal cell in culture medium under conditions suitable for the production of the polyketide; and
   (c) isolating a fraction of culture medium containing the polyketide.

8. The method of claim 7 wherein the polyketide is a statin.

9. The method of claim 8 wherein the statin is a lovastatin.

10. The method of any one of claims 7, 8 and 9 wherein the fungal cell is genetically modified to overexpress CreA.

11. The method of claim 10 wherein the fungal cell is an *Ascomycete*.

12. The method of claim 11 wherein the *Ascomycete* is *A. terreus*.

13. A method for producing a polyketide, the method comprising:
   (a) culturing in culture medium under conditions suitable for the production of the polyketide a fungus that produces the polyketide and has been genetically modified to conditionally expresses CreA or a fungal homolog thereof, whereby the polyketide is produced; and (b) isolating a fraction of culture medium containing a polyketide.

14. The method of claim 13 wherein the polyketide is a statin.

15. The method of claim 14 wherein the statin is lovastatin.

16. The method of any one of claims 13, 14 and 15 wherein the fungus is an *Ascomycete*.

17. The method of claim 16 wherein the *Ascomycete* is *A. terreus*.

18. A method for producing a polyketide, the method comprising:

(a) culturing in culture medium under conditions suitable for the production of the polyketide a fungus that produces the polyketide and has been genetically modified to overexpress CreA or a fungal homolog thereof, whereby the polyketide is produced; and (b) isolating a fraction of culture medium containing the polyketide.

19. The method of claim 18 wherein the polyketide is a statin.

20. The method of claim 19 wherein the statin is a lovastatin.

21. The method of claim any one of claims 18, 19 and 20 wherein the fungus is an *Ascomycete*.

22. The method of claim 21 wherein the *Ascomycete* is *A. terreus*.

23. A method for producing a statin, the method comprising:

(a) culturing in culture medium under conditions suitable for the production of the statin a fungus that produces the statin and has been genetically modified to conditionally express CreA or a fungal homolog thereof, whereby the statin is produced; and (b) isolating a fraction of culture medium containing a statin.

24. The method of claim 23 wherein the statin is lovastatin.

25. The method of claim 23 or 24 wherein the fungus is an *Ascomycete*.

26. The method of claim 23 or 24 wherein the fungus is *A. terreus*.

27. A method for producing a statin, the method comprising:

(a) culturing in culture medium under conditions suitable for the production of the statin a fungus that produces the statin and has been genetically modified to overexpress CreA or a fungal homolog thereof, whereby the statin is produced; and (b) isolating a fraction of culture medium containing the statin.

28. The method of claim 27 wherein the statin is lovastatin.

29. The method of claim 27 or 28 wherein the fungus is an *Ascomycete*.

30. The method of claim 27 or 28 wherein the fungus is *A. terreus*.

31. A method for modulating the production of a polyketide produced by *A. terreus*, the method comprising conditionally expressing CreA or a fungal homolog thereof in *A. terreus*, whereby the production of the polyketide is modulated.

32. The method of claim 31 comprising conditionally expressing CreA.

33. The method of claim 31 wherein the polyketide is a statin.

34. The method of claim 33 wherein the statin is lovastatin.

35. The method of any one of claims 31, 33 and 34 wherein the production of polyketide by *A. terreus* is increased.

36. A method for producing a polyketide, the method comprising culturing in culture medium under conditions suitable for the production of the polyketide a genetically modified *A. terreus* that produces the polyketide and conditionally expresses CreA or a fungal homolog thereof, whereby the polyketide is produced.

37. The method of claim 36 wherein the polyketide is a statin.

38. The method of claim 37 wherein the statin is lovastatin.

39. The method of any one of claims 36, 37, and 38 further comprising isolating a fraction of culture medium containing the polyketide.

40. A method for modulating the production of a polyketide produced by *A. terreus*, the method comprising overexpressing CreA or a fungal homolog thereof in *A. terreus*, whereby the production of the polyketide is modulated.

41. The method of claim 40 comprising overexpressing CreA.

42. The method of claim 40 wherein the polyketide is a statin.

43. The method of claim 42 wherein the statin is lovastatin.

44. The method of any one of claims 40, 42 and 43 wherein the production of a polyketide by *A. terreus* is increased.

45. The method of any one of claims 40, 42, 43, 31, 33 and 34 wherein production of the polyketide is increased.

46. The method of any one of claims 40, 42, 43, 31, 33 and 34 wherein production of the polyketide is decreased.

47. A method for producing a polyketide, the method comprising culturing in culture medium under conditions suitable for the production of the polyketide a genetically modified *A. terreus* that produces the polyketide and overexpresses CreA or a fungal homolog thereof, whereby the polyketide is produced.

48. The method of claim 47 wherein the polyketide is a statin.

49. The method of claim 48 wherein the statin is lovastatin.

50. The method of any one of claims 47, 48 and 49 further comprising isolating a fraction of culture medium containing a polyketide.

* * * * *

UNITED STATES PATENT AND TRADEMARK OFFICE
CERTIFICATE OF CORRECTION

PATENT NO. : 6,949,356 B1
APPLICATION NO. : 09/487558
DATED : September 27, 2005
INVENTOR(S) : Robert Busby et al.

It is certified that error appears in the above-identified patent and that said Letters Patent is hereby corrected as shown below:

Title Page, Under Inventors item (75), line 4, replace "Plan" with --Plain--

Title Page, item (56) col. 2, Line 30 "Bentley" publication, replace "Crt." with --Crit.--

Title Page, item (56) col. 2, Line 31 "Boret" publication, replace "Boret" with --Borel--

On Title Page 2, item 56, col. 1, Line 4 "Cardenas" publication, replace "immunouppressant" with --immunosuppressant--

Page 2, item 56 col. 1, Line 11 "Chen" publication, replace "(1983)" with --(1993)--

Page 2, item 56 col. 1, Line 22 "Douglas" publication, replace "-62-" with -- -β--

Page 2, item 56 col. 1, Line 60 "Mingot" publication, replace "Monoxygenase" with --Monooxygenase--

Page 2, item 56 col. 2, Line 6 "Nelisssen" publication, replace "Nelisssen" with --Nelissen--

Page 2, item 56 col. 2, Line 32 "Qadota" publication, replace "subnit" with --subunit--

On Title Page 2, item 56 col 2., Line 35 and 36 "Ravid" publication, replace "Imparied" with --Impaired--; and replace "3methylglutary" with --3methylglutaryl--

Col. 1, line 4, replace "119(c)" with --119(e)--

Col. 3, line 21, after "that" delete "a"

Col. 13, line 24, replace "ergocominine" with --ergocorninine--

Col. 20, line 32, replace "ergocominine" with --ergocorninine--

Col. 23, line 39, replace "A" with --An--

Col. 24, line 30, replace "ergocominine" with --ergocorninine--

Col. 29, line 53, replace "ergocominine" with --ergocorninine--

Col. 31, line 45, replace "MSS1" with --MSS11--

UNITED STATES PATENT AND TRADEMARK OFFICE
CERTIFICATE OF CORRECTION

PATENT NO. : 6,949,356 B1
APPLICATION NO. : 09/487558
DATED : September 27, 2005
INVENTOR(S) : Robert Busby et al.

It is certified that error appears in the above-identified patent and that said Letters Patent is hereby corrected as shown below:

Col. 35, line 53, replace "ergocominine" with --ergocorninine--

Col. 37, line 3, replace "STE2" with --STE12--

Col. 39, line 14, after "protein" replace "A" with --An--

Col. 40, line 6, replace "ergocominine" with --ergocorninine--

Col. 43, line 53, replace "ergocominine" with --ergocorninine--

Col. 50, line 58, replace "63: 33414" with --63: 3341-4--

Col. 51, line 2, replace "leu2Δ1/leu2Δ0" with --1eu2Δ0/leu2Δ0--

Col. 58, line 39, after "fungal" replace "cells" with --cell--

Signed and Sealed this

Fifth Day of December, 2006

JON W. DUDAS
*Director of the United States Patent and Trademark Office*